(12) United States Patent
Lorenz et al.

(10) Patent No.: US 11,432,736 B2
(45) Date of Patent: Sep. 6, 2022

(54) SIMPLIFIED NAVIGATION OF SPINAL MEDICAL IMAGING DATA

(71) Applicant: KONINKLIJKE PHILIPS N.V., Eindhoven (NL)

(72) Inventors: Cristian Lorenz, Hamburg (DE); Peter Bornert, Hamburg (DE); Tobias Klinder, Uelzen (DE)

(73) Assignee: Koninklijke Philips N.V., Eindhoven (NL)

( * ) Notice: Subject to any disclaimer, the term of this patent is extended or adjusted under 35 U.S.C. 154(b) by 561 days.

(21) Appl. No.: 16/465,629

(22) PCT Filed: Dec. 5, 2017

(86) PCT No.: PCT/EP2017/081558
§ 371 (c)(1),
(2) Date: May 31, 2019

(87) PCT Pub. No.: WO2018/104322
PCT Pub. Date: Jun. 14, 2018

(65) Prior Publication Data
US 2020/0022609 A1   Jan. 23, 2020

(30) Foreign Application Priority Data
Dec. 8, 2016   (EP) .................................. 16202955

(51) Int. Cl.
*A61B 5/055*   (2006.01)
*A61B 5/00*    (2006.01)
(Continued)

(52) U.S. Cl.
CPC ............ *A61B 5/055* (2013.01); *A61B 5/4566* (2013.01); *A61B 6/032* (2013.01); *A61B 6/463* (2013.01);
(Continued)

(58) Field of Classification Search
CPC ....... A61B 5/055; A61B 5/4566; A61B 6/032; A61B 6/463; A61B 6/505; A61B 6/5223;
(Continued)

(56) References Cited

U.S. PATENT DOCUMENTS 10,032,296 B2   7/2018 Klinder et al.
2007/0133849 A1   6/2007 Young et al.
(Continued)

OTHER PUBLICATIONS

Vrtovec, Tomaž, et al. "Automated generation of curved planar reformations from MR images of the spine." Physics in medicine and biology 52.10 (2007): 2865.
(Continued)

*Primary Examiner* — Peter Luong

(57) ABSTRACT

The invention provides for a medical imaging system (700) comprising: a memory (734) for storing machine executable instructions (740), a display (732) for rendering a user interface (800), and a processor (730). Execution of the machine executable instructions causes the processor to receive (1000) three dimensional medical image data (746) descriptive of a region of interest (709) of a subject (718). The region of interest comprises a spine (200). Execution of the machine executable instructions further causes the processor to receive (1002) a set of spinal coordinate systems (748) each descriptive of a location and an orientation of spinal vertebrae in the three dimensional medical image data. The set of spinal coordinate systems further comprises a set of spine centerline positions (102) each positioned on a spine centerline (108). Execution of the machine executable instructions further causes the processor to receive (1004) a mapping (750) between the set of spinal coordinate systems and a simplified coordinate system. The simplified coordinate system comprises a spinal height (300) descriptive of a position along the spine centerline. The simplified coordinate system further comprises a rotational orientation
(Continued)

relative to a local vertebrae orientation. The simplified coordinate system further comprises an offset from the spine centerline. Execution of the machine executable instructions further cause the processor to repeatedly receive (1006) a simplified coordinate (752) of the simplified coordinate system from the user interface. Execution of the machine executable instructions further cause the processor to repeatedly calculate (1008) a spinal image rendering (754). Calculating the spinal image rendering comprises using the mapping to transform the simplified coordinate into the set of spinal coordinate systems to determine an image location in the three dimensional medical image data. Execution of the machine executable instructions further cause the processor to repeatedly render (1010) the spinal image rendering on the display.

15 Claims, 15 Drawing Sheets

(51) Int. Cl.
*A61B 6/03* (2006.01)
*A61B 6/00* (2006.01)
*G06T 19/00* (2011.01)
*G01R 33/50* (2006.01)
*G01R 33/56* (2006.01)

(52) U.S. Cl.
CPC ............ *A61B 6/505* (2013.01); *A61B 6/5223* (2013.01); *G06T 19/00* (2013.01); *G01R 33/50* (2013.01); *G01R 33/5608* (2013.01); *G06T 2210/41* (2013.01); *G06T 2219/008* (2013.01); *G06T 2219/028* (2013.01)

(58) Field of Classification Search
CPC ............... G06T 19/00; G06T 2210/41; G06T 2219/008; G06T 2219/028; G01R 33/50; G01R 33/5608
See application file for complete search history.

(56) References Cited

U.S. PATENT DOCUMENTS

| | | |
|---|---|---|
| 2008/0287796 A1 | 11/2008 | Kraly et al. |
| 2012/0053454 A1 | 3/2012 | Wang et al. |
| 2013/0202179 A1 | 8/2013 | Illes et al. |
| 2014/0341547 A1 | 11/2014 | Shenoy et al. |
| 2015/0131881 A1 | 5/2015 | Gnanamani et al. |
| 2016/0089074 A1* | 3/2016 | Wang ............... G16H 50/30 600/407 |
| 2016/0260231 A1 | 9/2016 | Klinder et al. |

OTHER PUBLICATIONS

Klinder et al "Automated Model-Based Vertebra Detection, Identificaiton, and Segmentation in CT Images" Medical Imaging Analysis, Oxford University Press, vol. 13, No. 3, Feb. 20, 2009 p. 471-482.

Vrtovec, Tomaž, et al. "Automated curved planar reformation of 3D spine images." Physics in medicine and biology 50.19 (Oct. 7, 2005): p. 4527-4540.

Forsberg et al "Fully Automatic Measurements of Axial Vertebral Rotation for Assessment of Spinal Deformity in Idiopathic Scoliosis.." Physics in Med. and Biol. vol. 58, No. 6, Feb. 26, 2013 p. 1775-1787.

Search Report dated Mar. 1, 2018.

* cited by examiner

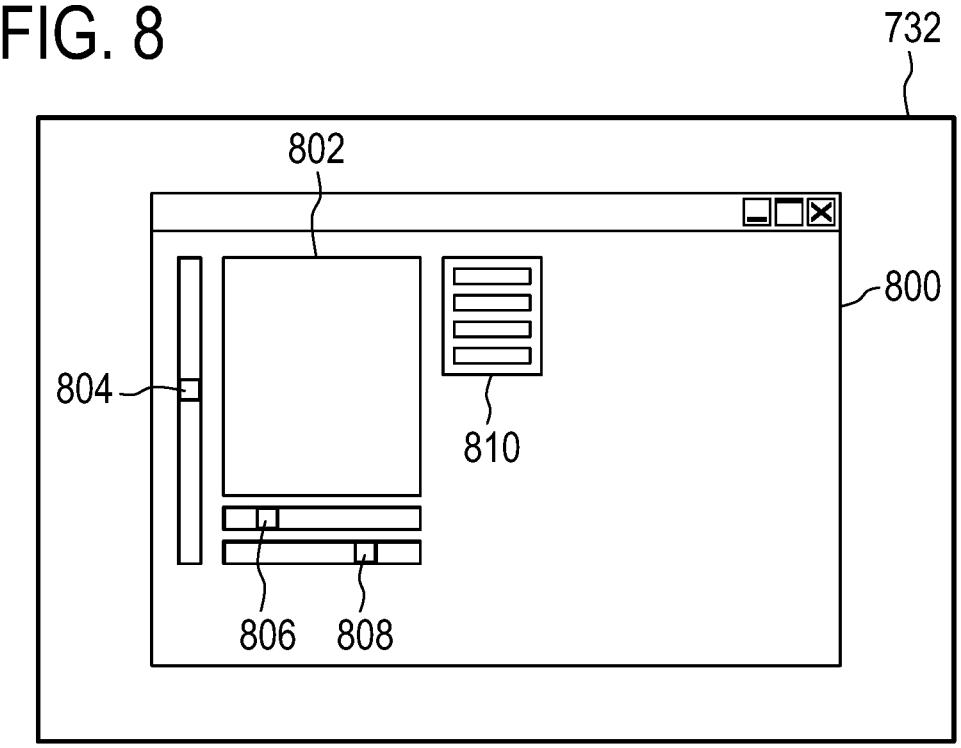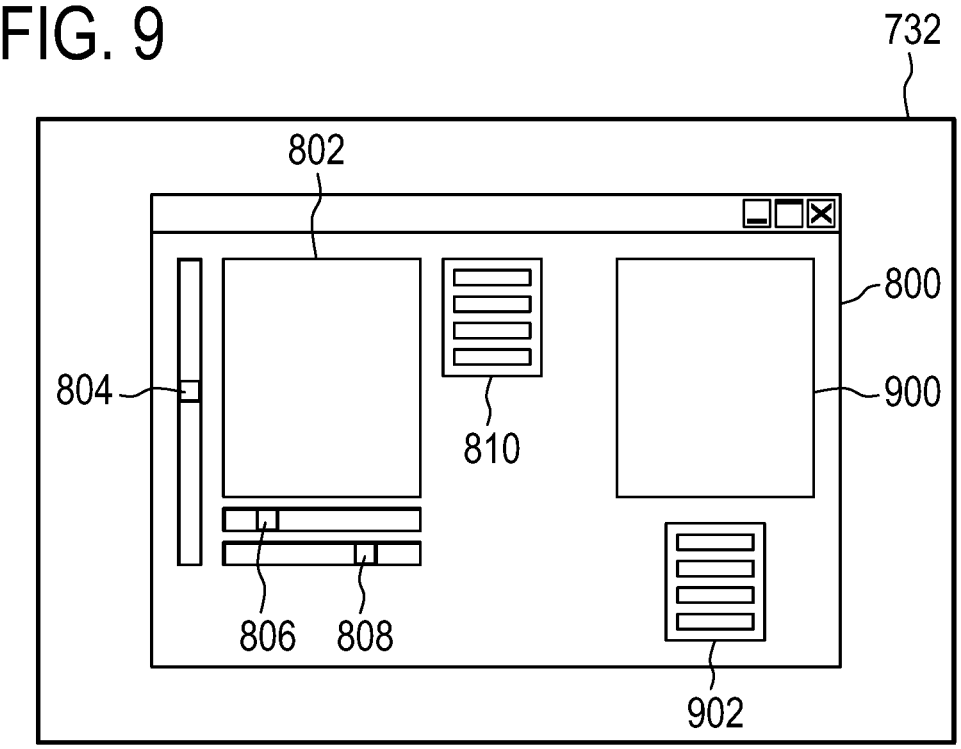

US 11,432,736 B2

SIMPLIFIED NAVIGATION OF SPINAL MEDICAL IMAGING DATA

CROSS REFERENCE TO RELATED APPLICATIONS

This application is a U.S. national phase application of International Application No. PCT/EP2017/081558 filed on Dec. 5, 2017, which claims the benefit of EP Application Serial No. 16202955.7 filed on Dec. 8, 2016 and is incorporated herein by reference.

FIELD OF THE INVENTION

The invention relates to medical imaging and magnetic resonance imaging, in particular to medical imaging of the spine.

BACKGROUND OF THE INVENTION

A large static magnetic field is used by Magnetic Resonance Imaging (MRI) scanners to align the nuclear spins of atoms as part of the procedure for producing images within the body of a patient. This large static magnetic field is referred to as the B0 field.

During an MRI scan, Radio Frequency (RF) pulses generated by one or more transmitter coils cause a called B1 field. Additionally applied gradient fields and the B1 field cause perturbations to the effective local magnetic field. RF signals are then emitted by the nuclear spins and detected by one or more receiver coils. These RF signals are used to construct the MR images. These coils can also be referred to as antennas.

MRI scanners are able to construct images of either slices or volumes. A slice a thin volume that is only one voxel thick. A voxel is a small volume element over which the MR signal is averaged, and represents the resolution of the MR image. A voxel may also be referred to as a pixel (picture element) herein if a single slice is considered.

MRI techniques can be used to image various anatomical structures within a subject. The journal article Vrtovec, Tomaž, et al. "Automated generation of curved planar reformations from MR images of the spine." Physics in medicine and biology 52.10 (2007): 2865 describes a method for generating curved planar reformation (CPR) images of the spine using MRI (hereafter "Vrtovec et. al.").

SUMMARY OF THE INVENTION

The invention provides for a medical imaging system, a computer program product, and a method in the independent claims. Embodiments are given in the dependent claims.

The spine comprises individual vertebra, which are movable, to some degree, with respect to each other. Navigating medical image data to find particular views of specific anatomical structures can be difficult and may involve trial and error on the part of the operator. Embodiments may streamline this process, or even completely eliminate the trial and error involved by providing for navigation of the spine using a simplified coordinate system. The simplified coordinate system can be defined in terms of a spinal height, which is equivalent to a particular location along a spine centerline, a rotation about the spine centerline, and an offset from the spine centerline.

An individual coordinate system can be defined for each of the vertebrae forming a set of spinal coordinate systems. A mapping between the simplified coordinate system and the spinal coordinate system provides a spatial orientation for rotations and offsets about the spine centerline. The operator can also select one or more views of the spine to display which are referenced to the selected simplified coordinates. For example, a CPR image can be used for interactively navigating the three dimensional medical imaging data and then the operator can select the type of image to be displayed.

A further potential advantage of using such an interactive and simplified coordinate system is that the simplified coordinate system its self may serve as a registration between various three dimensional medical imaging data sets containing data descriptive of the spine. This could for example be used to quickly and efficiently compare medical imaging data sets imaged at different times of the same subject. An operator or an segmentation algorithm could consistently define the set of spinal coordinate systems. This would be sufficient to enable an operator to define registrations or particular simplified coordinate locations that are of interest. The operator identifies a simplified coordinate in one image and then the simplified coordinates in another image can be used to automatically generate the same view.

Such an arrangement may also be of use for comparing three dimensional medical imaging data from different subjects. For example the spinal height could be based on a scaled dimension relative to the closest vertebrae. The spinal height would then be independent of absolute distances and would be anatomically neutral. This could for example enable the identification of anatomical locations (and views) in the simplified coordinates using reference three dimensional medical imaging data. Once the set of spinal coordinate systems are defined these views could potentially be recalled for other three dimensional medical imaging data sets of other subjects automatically.

In one aspect the invention provides for a medical imaging system comprising a memory for storing machine-executable instructions. The medical imaging system further comprises a display for rendering a graphical user interface. The medical imaging system further comprises a processor for controlling the medical imaging system.

Execution of the machine-executable instructions cause the processor to receive three-dimensional medical image data descriptive of a region of interest of a subject. The region of interest comprises a spine. Execution of the machine-executable instructions further cause the processor to receive a set of spatial coordinate systems each descriptive of the location and orientation of spinal vertebrae in the three-dimensional medical image. Spinal vertebrae are bony like structures that make up the hard or rigid portion of a spine. The spinal coordinate systems may for example each describe the location and orientation of a spinal vertebra of the spine. The set of spinal coordinate systems further comprises a set of spine center line positions each descriptive of a position along a spine center line. The set of spine center line positions may for instance be part of the set of spinal coordinate systems. For example each of the spinal vertebrae may define a point which is indicated as a spine center line position and then have other features or coordinate systems which are used to define the set of spinal coordinate systems in terms of this spine center line position.

Execution of the machine-executable instructions further cause the processor to receive a mapping between the set of spinal coordinate systems and a simplified coordinate system. The simplified coordinate system comprises a spinal height descriptive of a position along the spine center line. The simplified coordinate system further comprises a rotational orientation relative to a local vertebrae orientation.

The local vertebrae orientation may for example be one of the set of spinal coordinate systems. The simplified coordinate system further comprises an offset from the spine center line. A difficulty when navigating three-dimensional images of the spine is that the spine is flexible and the spinal vertebrae can be slightly rotated or tilted with respect to each other. Using a normal three-dimensional coordinate system it may be very tricky to specify or find particular views of the spine in the three-dimensional medical image data. The simplified coordinate system may reduce the number of operations it takes for an operator to arrive at a particular view in the spine. The simplified coordinate system may also function as a de facto registration between one three-dimensional medical image data of a particular spine and another.

The spine center lines and the set of spinal coordinates for example may be defined in terms of landmarks or easily identifiable features in spinal vertebrae. A person or a segmentation algorithm could easily define the position of the spine center line positions and the associated set of spinal coordinate systems consistently for the same spine in different three-dimensional medical image datasets.

Once the simplified coordinates have been identified in one three-dimensional medical image dataset an operator could load a three-dimensional image dataset of the spine of the same person and could consistently go to the same view in different acquisitions of the medical image data. Another further advantage of the simplified coordinate system is that it may also assist in comparing the spines of different individuals or subjects. For example once the set of spinal coordinate systems and the mapping between them and the simplified coordinate system is established the coordinates in different individuals should show the same view and relative position along the spine. This for example may enable an operator to pull up a particular view of the spine consistently without having to manually navigate the three-dimensional medical image data.

Execution of the machine-executable instructions further cause the processor to repeatedly receive a simplified coordinate of the simplified coordinate system from the graphical user interface. Execution of the machine-executable instructions further cause the processor to repeatedly calculate a spinal image rendering. The calculation of the spinal image rendering comprises using the mapping to transform the simplified coordinates into the set of spinal coordinate systems to determine an image location in the three-dimensional medical image data. Execution of the machine-executable instructions further cause the processor to repeatedly render the spinal image rendering on a display. The three above steps are descriptive of a loop of the machine-executable instructions where the operator is able to easily navigate the three-dimensional medical image data using the simplified coordinate which are provided for the simplified coordinate system.

The user interface receives the simplified coordinate. The mapping then transforms this to the set of spinal coordinate systems. This is then used to reference a coordinate in terms of the three-dimensional medical image data. The three-dimensional medical image data may for instance be defined in terms of a Cartesian coordinate system. The set of spinal coordinate systems are coordinate systems which are located and orientated in space within the inherent coordinate system of the three-dimensional medical image data.

The advantages of this medical imaging system may comprise a reduced burden on an operator when navigating the three-dimensional medical image data.

In another embodiment, the receiving of the three-dimensional medical image data may be performed for example by receiving input from the graphical user interface where the operator identifies the location and orientation of various spinal vertebrae. In another embodiment, the receiving of the set of spinal coordinate systems is performed by a segmentation algorithm.

In another embodiment, the receiving of the mapping between the set of spinal coordinate systems and the simplified coordinate system may comprise defining how the simplified coordinate system relates to the individual set of spinal coordinates. The set of spinal coordinate systems may for example define the position and orientation of multiple spinal vertebrae. As an operator navigates up and down the spine center line the closest vertebrae to this position are the relevant spinal coordinate systems. Different methods can be envisaged for doing this mapping. For example there may be abrupt changes in the use of which coordinate for which vertebrae is used. In other examples, the distance between the two closest spine center line positions could be used to take an average between the closest spinal coordinate systems.

In another embodiment, execution of the machine-executable instructions further cause the processor to repeatedly receive an image rendering type selection from the user interface. Execution of the machine-executable instructions further causes the processor to repeatedly recalculate a spinal image rendering using the image rendering type selection. This embodiment may be beneficial because it may enable the operator to switch between various image rendering types and in some instances also to select multiple image rendering types to be displayed on the graphical user interface. This may be advantageous, for example, because there may be some image rendering types which display the spine in a manner which facilitates finding the proper anatomical landmarks or region for imaging. Once these landmarks have been found then an image rendering type which is of a type useful for a physician may be selected.

In another embodiment, the image rendering type is any one of the following: an orthographic view with a freely chosen axes, an orthographic view with axis aligned with the three-dimensional data, an orthographic view with an axis aligned with the spinal center line position at the spinal coordinate.

There may be a variety of different image rendering types. For example one image rendering type may be a conventional unguided ortho-view. This may for example be free navigation and correspond to the orthographic view with freely chosen axes. In this example a view of the three-dimensional dataset is chosen and the axes are oriented arbitrarily. In another example there may be a spine guided ortho-view with the axes parallel to the axes inherent or defined in the three-dimensional medical image data. For example the simplified coordinates may be used to navigate but the view which is calculated or shown is still in terms of the coordinate system of the three-dimensional medical image data. This may correspond to the orthographic view with an axis aligned to the three-dimensional data. The orthographic view with an axis aligned with the spinal center line position at the spinal coordinate may take several variants. This may depend upon the type of plane which is used to slice the three-dimensional data. For example, this may correspond to a spine guided ortho-view which is oblique. A Cartesian coordinate system is used however a Cartesian coordinate system is defined by the closest or two closest sets of spinal coordinate systems.

One axis may for example be tangent with the spine center line. It is also envisioned that the plane which is used to cut the three-dimensional medical image data may not necessarily be a flat plane. There could be for example a plane that is distorted and follows the spine center line. This could for example be a half plenary format where the spine center line is projected into a view plane. In this case the curvature is still visible in the orthogonal view. In other examples this could correspond to a full planar reformat where the spine center line becomes a straight line. In both the half plenary format and the full plenary format there may be some distortions caused in the resultant image. However, either both of these two views may be extremely useful in identifying the exact location within the spine. For example the half plenary format or the full plenary format could be used by an operator to quickly navigate through the three-dimensional medical image data and then once the proper anatomical position is located switch to one of the other image rendering types.

In another embodiment, execution of the machine-executable instructions further cause the processor to receive a location registration selection from the user interface. Execution of the machine-executable instructions further cause the processor to store the simplified coordinate as an image registration. This may be beneficial because it may provide for efficient means of saving the registration which can be recalled from an image later or even applied to medical image data that contains the spine of the same subject or even different subjects.

The graphical user interface could for example have a button or widget on it which when pressed causes the simplified coordinate to be stored in a memory as the image registration.

In another embodiment, execution of the machine-executable instructions further cause the processor to receive additional three-dimensional image data descriptive of an additional region of interest of the subject. The subject may be the same or a different subject. The region of interest comprises the spine. The spine for example may be an identical spine imaged at a different time or it may be a spine from a different subject.

Execution of the machine-executable instructions further cause the processor to receive additional three-dimensional medical image data descriptive of the region of interest of the subject. The region of interest comprises the spine. Execution of the machine-executable instructions further cause the processor to receive an additional set of spinal coordinate systems equivalent to the set of spinal coordinate systems. Execution of the machine-executable instructions further cause the processor to receive an additional mapping. The additional mapping is between the additional set of spinal coordinate systems and the simplified coordinate system. This may be beneficial because this essentially registers the additional three-dimensional medical image data to the three-dimensional medical image data.

In another embodiment, execution of the machine-executable instructions further cause the processor to calculate an additional spinal image rendering. Calculating the additional spinal image rendering comprises using the additional mapping to transform the simplified coordinate into the additional set of spinal coordinate systems to determine an additional image location in the additional three-dimensional medical image data. In some examples the simplified coordinate may be the image registration and may be recalled from storage or memory. Execution of the machine-executable instructions further cause the processor to render the additional spinal image rendering on the display. This embodiment may be beneficial because it may enable an operator to easily display spinal images from multiple datasets easily without needing to navigate the second dataset.

In another embodiment, the set of spinal coordinates and the mapping is received as input from a user interface. For example, the operator may once using a conventional interface identify individual vertebrae and particular anatomical locations which enable a set of spinal coordinates to be determined.

In another embodiment, execution of the machine-executable instructions further cause the processor to calculate a segmentation of the three-dimensional medical image data using a segmentation algorithm. The segmentation algorithm may be according to standard segmentation algorithms which are able to identify the location and orientation of vertebrae. Execution of the machine-executable instructions further causes the processor to calculate the set of spinal coordinate systems and/or the mapping using the segmentation. This may be beneficial because it may enable the automatic generation of the set of spinal coordinate systems and also equivalently the mapping between the set of spinal coordinate systems and the simplified coordinate system.

In another embodiment, the three-dimensional medical image data is any one of the following: a three-dimensional dataset and a stack of two-dimensional slices.

In another embodiment, the medical imaging system further comprises a magnetic resonance imaging system. The memory further comprises pulse sequence commands. The pulse sequence commands comprise commands for controlling the magnetic resonance imaging system to acquire the three-dimensional medical image data according to a magnetic resonance imaging protocol. The three-dimensional image data is magnetic resonance imaging data. Execution of the machine-executable instructions further cause the processor to receive the three-dimensional medical image data by reconstructing the three-dimensional medical image data from the magnetic resonance data.

In another embodiment, the three-dimensional image data is any one of the following: a T1 weighted image, a T2 weighted image, and a composite T1 and T2 weighted image.

In another embodiment, the medical imaging system further comprises a computed tomography system.

In another embodiment, the three-dimensional image data is computed tomography image data.

In another aspect, the invention provides for a medical imaging method. The method comprises receiving three-dimensional medical image data descriptive of a region of interest of a subject. The region of interest comprises a spine. The method further comprises receiving a set of spinal coordinate systems each descriptive of a location and an orientation of spinal vertebrae in a three-dimensional medical image. The set of spinal coordinate systems further comprises a set of spine center line positions each descriptive of a position along a spine center line. The method further comprises receiving a mapping between the set of spinal coordinate systems and a simplified coordinate system. The simplified coordinate system comprises a spinal height descriptive of a position along the spine center line. The simplified coordinate system further comprises a rotational orientation relative to the local vertebrae orientation.

The simplified coordinate system further comprises an offset from the spine center line. The method further comprises repeatedly receiving a simplified coordinate of the simplified coordinate system from the graphical user interface. The method further comprises repeatedly calculating a spinal image rendering. The calculation of the spinal image rendering comprises using the mapping to transform the simplified coordinate into the set of spinal coordinate systems to determine an image location in the three-dimensional medical image data. The method further comprises repeatedly rendering the spinal image rendering on a display. The advantages of this method have been previously discussed.

In another embodiment, the method further comprises repeatedly receiving an image rendering type selection from the user interface. The method further comprises repeatedly recalculating the spinal image rendering using the image rendering type selection. The advantages of this method have been previously discussed.

In another aspect, the invention provides for a computer program product comprising machine-executable instructions for execution by a processor controlling the medical imaging system. The medical imaging system comprises a display for rendering a graphical user interface. Execution of the machine-executable instructions causes the processor to receive three-dimensional medical image data descriptive of a region of interest of a subject. The region of interest comprises a spine. Execution of the machine-executable instructions further causes the processor to receive a set of spinal coordinate systems each descriptive of a location and an orientation of spinal vertebrae in the three-dimensional medical image. The set of spinal coordinate systems further comprises a set of spine center line positions each descriptive of a position along a spine center line. Execution of the machine-executable instructions further causes the processor to receive a mapping between the set of spinal coordinate systems and a simplified coordinate system. The simplified coordinate system comprises a spinal height descriptive of a position along the spine center line. The simplified coordinate system further comprises a rotational orientation relative to a local vertebrae orientation. The simplified coordinate system further comprises an offset from the spine center line.

Execution of the machine-executable instructions further causes the processor to repeatedly receive a simplified coordinate of the simplified coordinate system from the graphical user interface. Execution of the machine-executable instructions further cause the processor to repeatedly calculate a spinal image rendering. The calculation of the spinal image rendering comprises using the mapping to transform the simplified coordinate into the set of spinal coordinate systems to determine an image location in the three-dimensional medical image data. Execution of the machine-executable instructions further cause the processor to render the spinal image rendering on a display. The advantages of this computer program product have been previously discussed.

In another embodiment, execution of the machine-executable instructions further cause the processor to repeatedly receive an image rendering type selection from the user interface. Execution of the machine-executable instructions further cause the processor to repeatedly recalculate a spinal image rendering using the image rendering type selection. The advantages of this embodiment have been previously discussed.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage may be any volatile or non-volatile computer-readable storage medium.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the C programming language or similar programming languages and compiled into machine executable instructions. In some instances the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, bluetooth connection, wireless local area network connection, TCP/IP connection, ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) display, Electroluminescent display (ELD), Plasma display panel (PDP), Liquid crystal display (LCD), Organic light-emitting diode display (OLED), a projector, and Head-mounted display.

Three dimensional medical image data as used herein is either a three dimensional image data set or a collection of two dimensional image data sets that are descriptive of a subjects anatomy.

Magnetic Resonance (MR) data is defined herein as being the recorded measurements of radio frequency signals emitted by atomic spins using the antenna of a magnetic resonance apparatus during a magnetic resonance imaging scan. Magnetic resonance data is an example of medical imaging data. A Magnetic Resonance (MR) image is defined herein as being the reconstructed two or three dimensional visualization of anatomic data contained within the magnetic resonance imaging data.

BRIEF DESCRIPTION OF THE DRAWINGS

In the following preferred embodiments of the invention will be described, by way of example only, and with reference to the drawings in which:

FIG. 8 illustrates a view of a graphical user interface;

FIG. 9 illustrates an alternative view of the graphical user interface of FIG. 8;

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
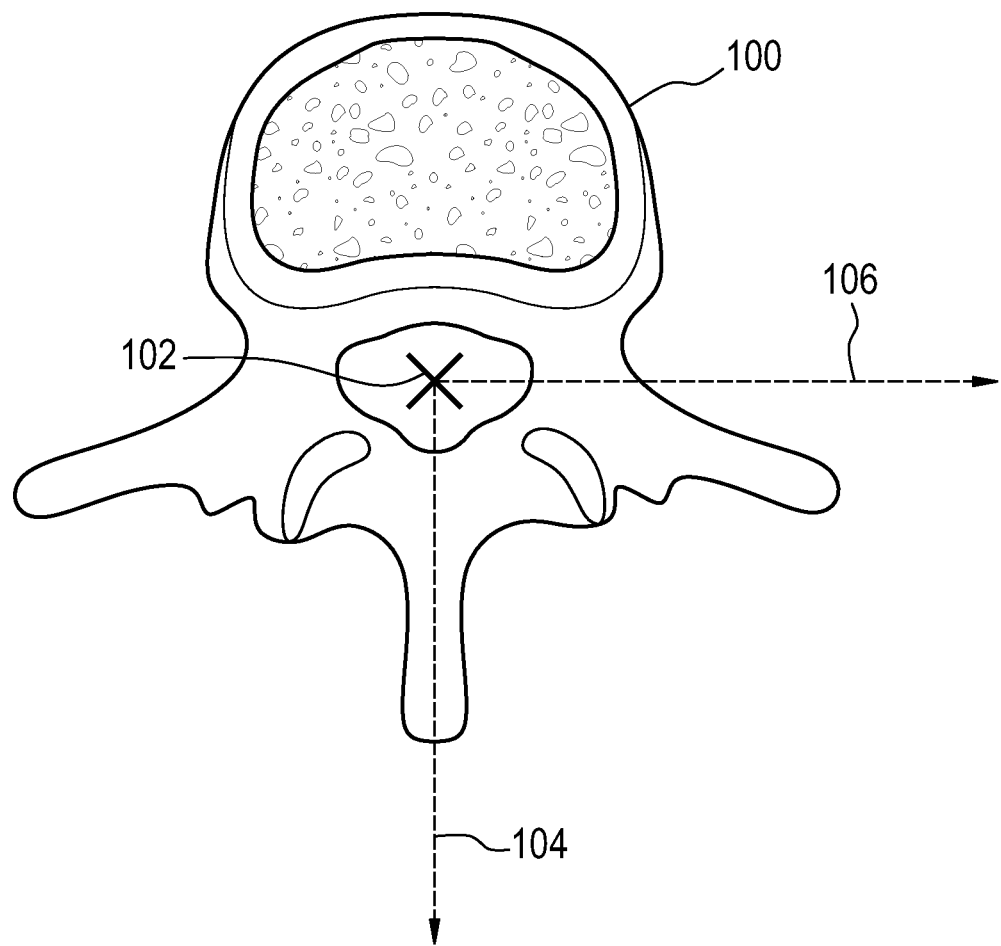
FIG. 1 illustrates a vertebrae.

FIG. 1 shows a view of a single vertebrae 100. The vertebrae 100 is a bony structure. The structure of the vertebrae enables the definition of a spinal coordinate system for each individual vertebrae 100. Using anatomical landmarks an image registration system for an individual can for example place the position of a center line or spine center line position 102. The symmetry of the vertebrae 100 can then be used to define a complete coordinate system. In this example there is a first axi 104 which defines an anterior-posterior direction. There is a second axis 106 that defines a left-right direction. There may be a third axi which is perpendicular to both the first axis 104 and the second axis 106 but is however not shown in this Fig.

Figure 2:
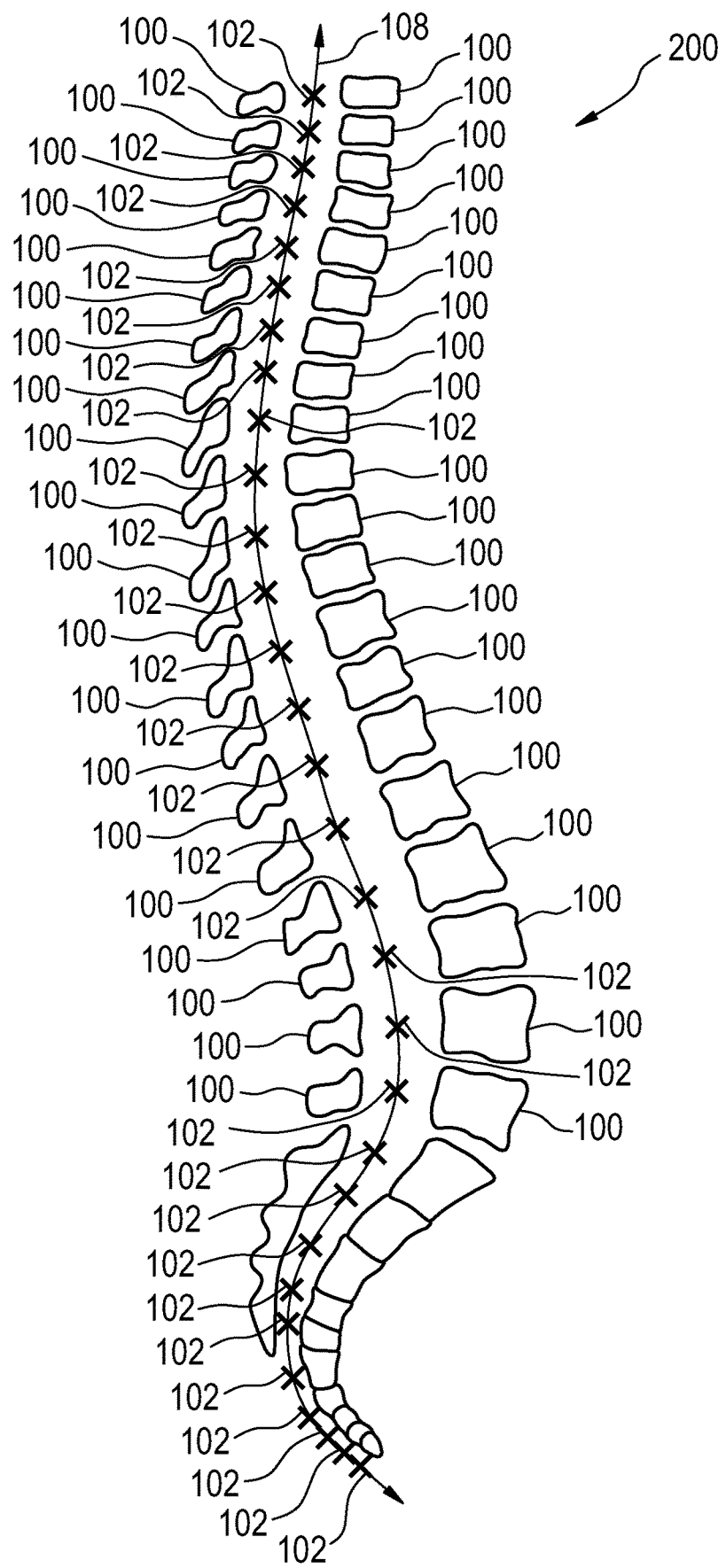
FIG. 2 illustrates a view of a spine and a spine centerline.

FIG. 2 shows an illustration which represents a cross-sectional view of an entire spine 200 which is made up of individual vertebrae 100. The location of the individual spine center line positions 102 is indicated. Each of the vertebrae 100 indicated in FIG. 2 may have its own coordinate system as is indicated in FIG. 1. The multiple spine center line positions 102 may be used for example for identifying a spine 108. During the navigation of three-dimensional medical image data which represents the spine 200 the spine center line 108 can be used as part of a coordinate system. A reference point can be taken on the spine center line 108 and a distance above and below this position can be defined. The individual set of spinal coordinate systems as is illustrated for a single spinal coordinate system in FIG. 1 can be used to provide an orientation about the spine center line 108. For example as the operator navigates up and down the spine center line 108 an orientation can be taken for using the axis 104 and/or 106. A rotation of the view taken can be taken about the spine center line 108 using it as an axis. An offset using the local spinal coordinate system can be defined in terms of an offset in the direction of the first axis 104 and/or the second axis 106.

When looking at the three-dimensional medical image data a variety of different views can be used to examine the data. FIGS. 3-6 are used to illustrate several different types of views.

Figure 3:
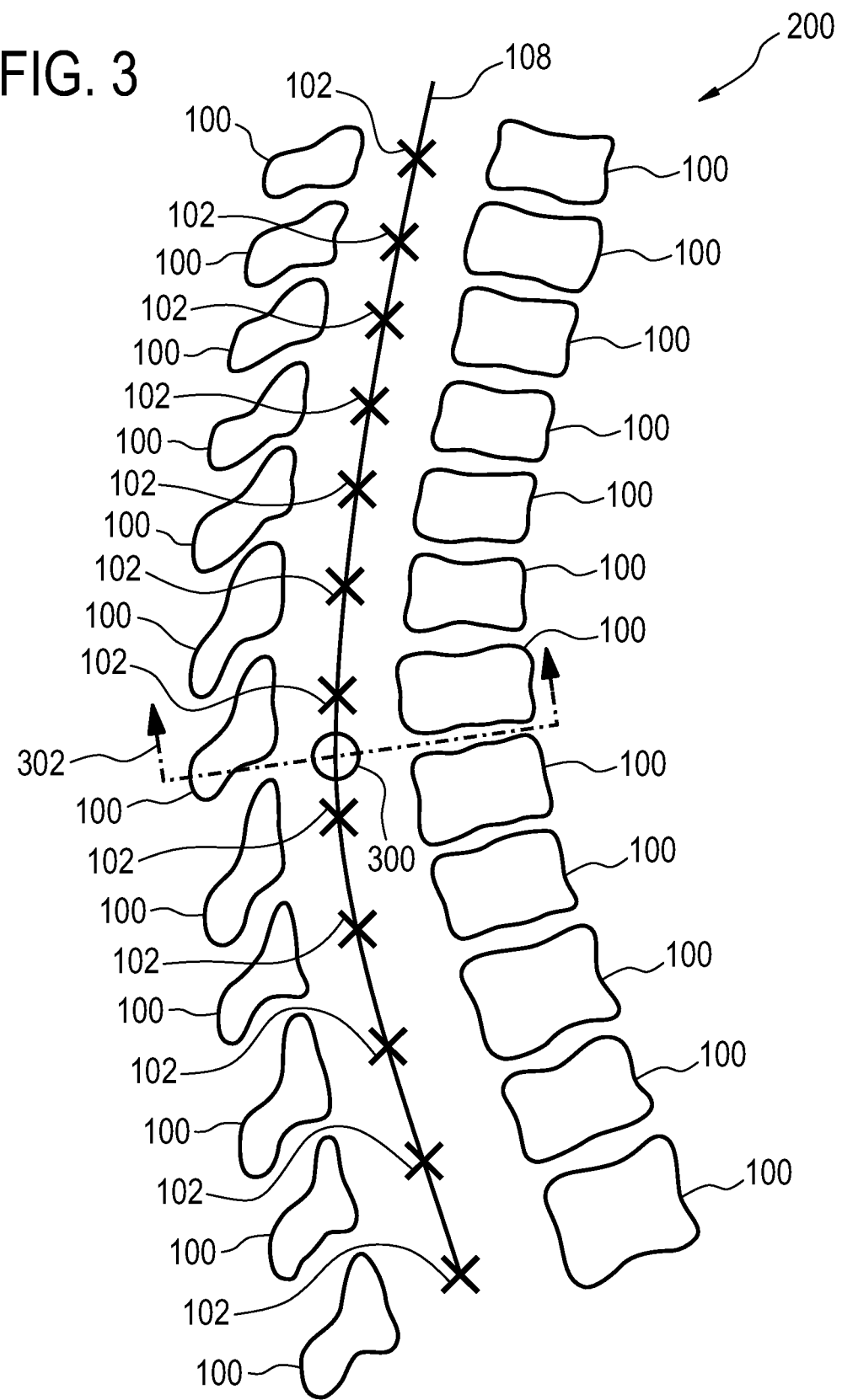
FIG. 3 shows a close-up of the spine of FIG. 2 to illustrate to positioning of an image view.

FIG. 3 represents one type of view which can be selected. The circle 300 indicates at its center a position along the spine center line 108. This position is referred to as the spinal height 300. The dashed line 302 with arrows indicates a view plane 302 which is used to slice the three-dimensional data for creating a rendering or two-dimensional view of the three-dimensional medical image data. In this example the view plane 302 is positioned such that it passes through the spinal height 300 and is perpendicular to the spine center line 108. It essentially shows a cross-sectional view that is perpendicular to the spine center line 108. This view could for example be modified by changing the directionality of the view 302 to look downwards.

Figure 4:
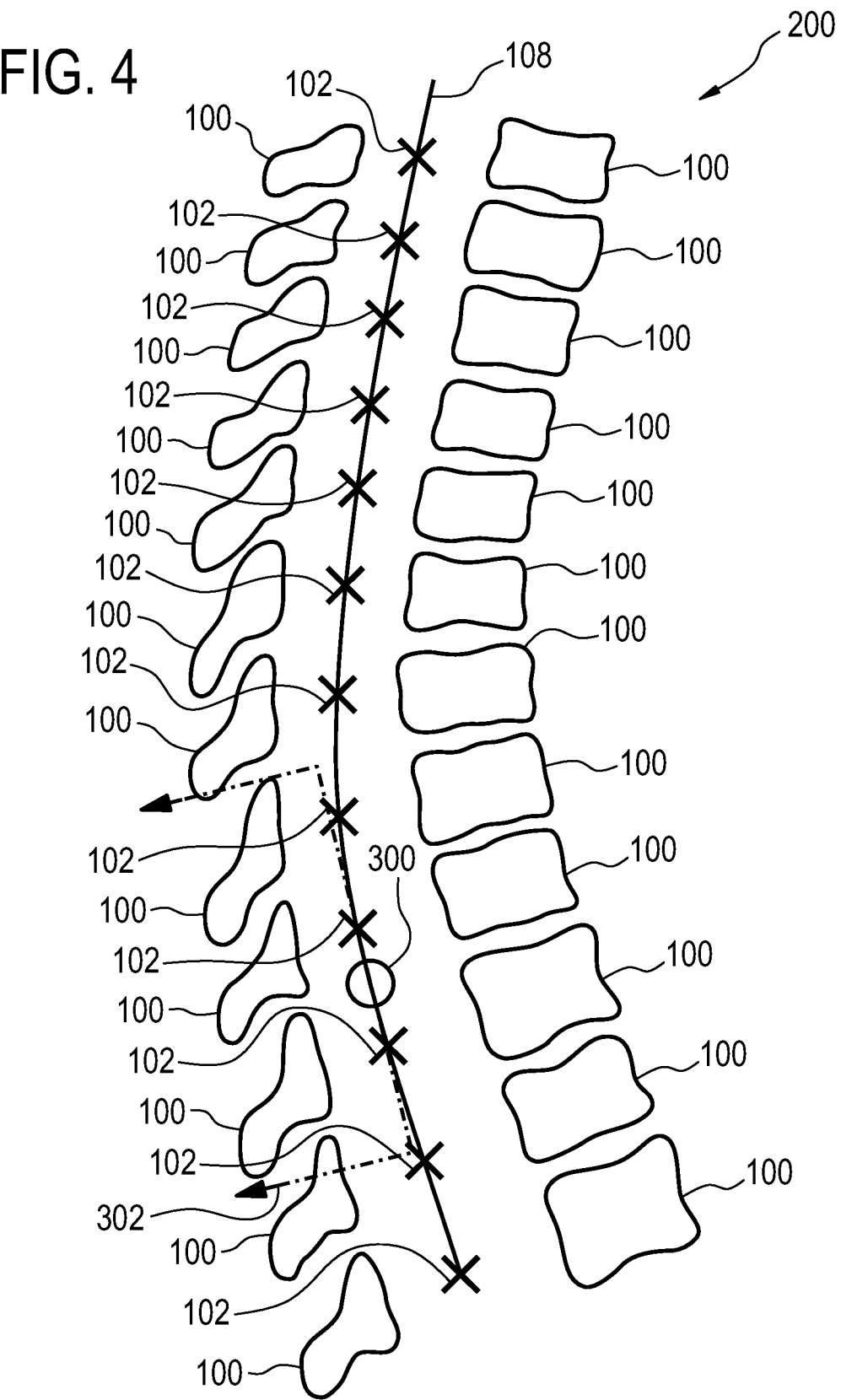
FIG. 4 shows a close-up of the spine of FIG. 2 to illustrate an alternative positioning of the image view.

FIG. 4 shows a view similar to that shown in FIG. 3 except the view plane 302 has been moved to a different position. The view plane 302 still passes through the spinal height 300. The view plane in this case is aligned such that it is parallel to the tangent of the spine center line 108. The rendering may be created by cutting the three-dimensional data at the position indicated by the view plane 302. The example shown in FIG. 4 may for example present a spine guided ortho-view that is oblique.

Figure 5:
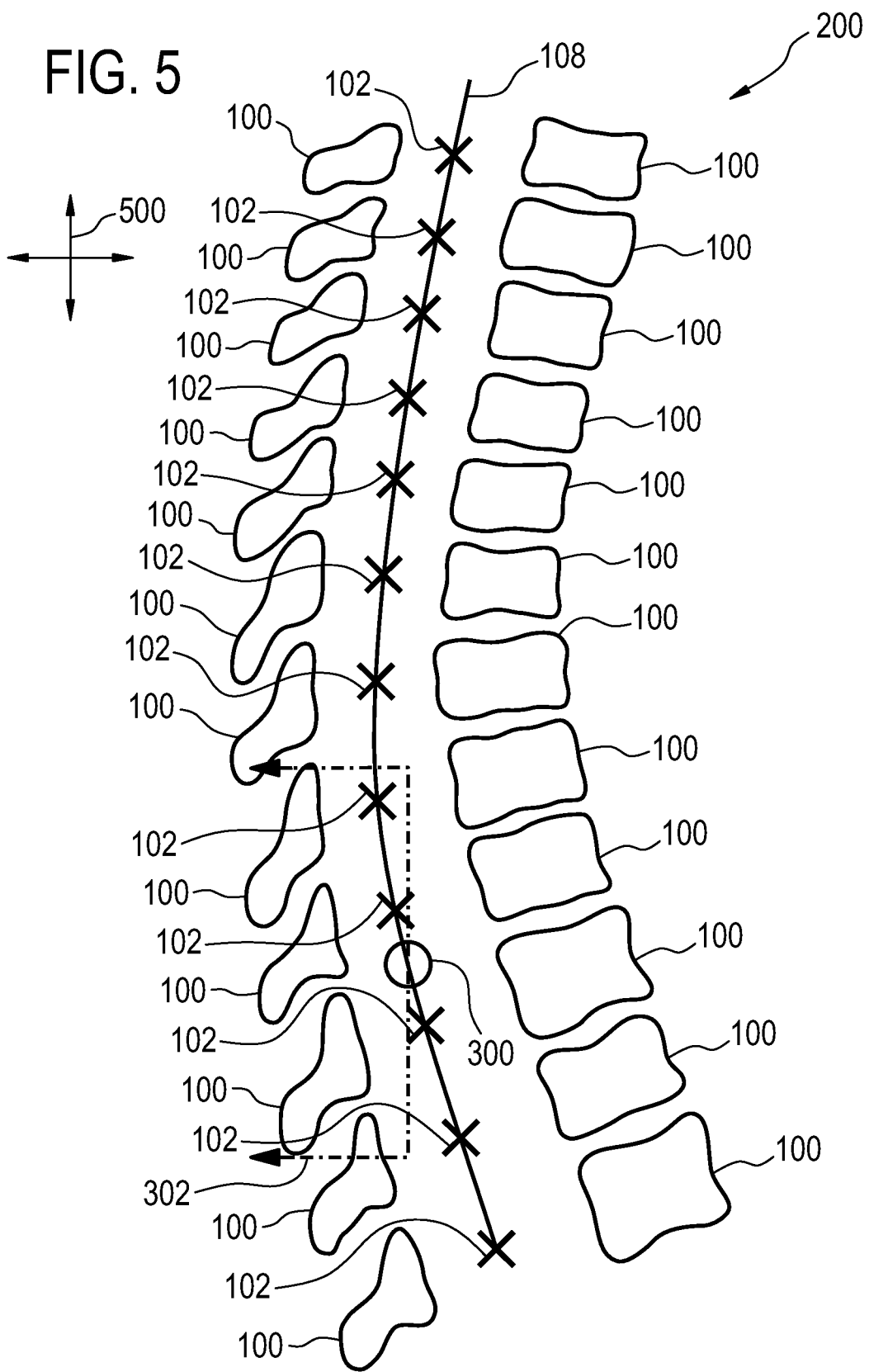
FIG. 5 shows a close-up of the spine of FIG. 2 to illustrate an alternative positioning of the image view.

FIG. 5 shows a further view of the spine 200 as was shown in FIGS. 3 and 4. In this example the view plane 302 has been moved or rotated with respect to the position it had in FIG. 4. In this example the plane still passes through the spinal height 300 but its orientation has been rotated such that it is parallel with a portion of a coordinate system 500 of the three-dimensional medical image data. This for example may be an example of a coordinate or view plane 302 used to generate a spine guided ortho-view with its axis parallel to the coordinate system 500 of the three-dimensional medical image data.

Figure 6:
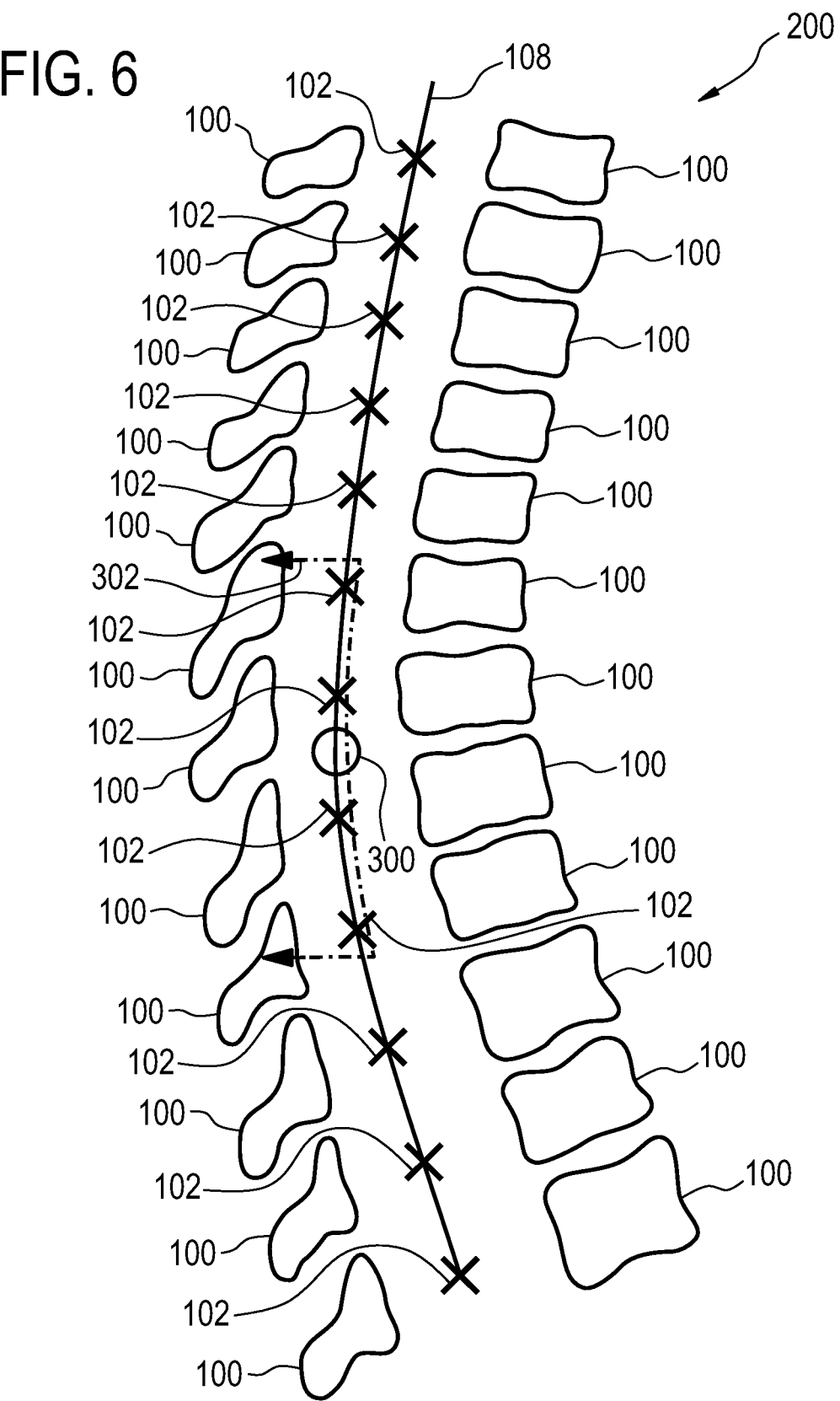
FIG. 6 shows a close-up of the spine of FIG. 2 to illustrate an alternative positioning of the image view.

FIG. 6 shows a further view of the spine 200 as is shown in FIGS. 3, 4, and 5. In this example the view plane 302 is again positioned differently. The view plane has been shown as being offset from the spine center line 108 to make it more visible in the FIG. n this case the view plane 302 is curved such that it follows the spine center line 108. The advantage of using such a plane is that the resulting rendering is in a coordinate system which is natural to the spine and is not affected by the position of the subject. This for example may be useful for generating a so called half planar reformat.

Using such a view plane may result in mild distortion of the image but it may make it easier for an operator to navigate the three-dimensional medical image data. The operator could then use for example the view created by the view plane 302 to find a location and then switch to another view by changing the location of the view plane 302 such as is shown in FIG. 3, 4, or 5. The example shown in FIG. 6 can also be further modified. The diagram in FIG. 6 shows that the spine center line 108 has a curvature to it. In reality the spine center line 108 may also go in and out of the paper such that the spine center line 108 takes a three-dimensional trajectory. A so called full planar reformat could also be created by correcting the data such that the spine center line 108 is always a straight up and down line in the rendering. In some cases this may result in strong distortion of the resulting medical image; however it may be extremely useful for selecting and identifying anatomical regions to image using other view plane 302 positions.

The orientation of the view plane 302 as is illustrated in FIGS. 3-6 essentially amounts to the selection of an image rendering type selection. The user interface could for example have a box or selector which enables an operator to select one or more different views to render. For a particular spinal height images in different directions and offsets could be conveniently created and rendered for an operator.

Figure 7:
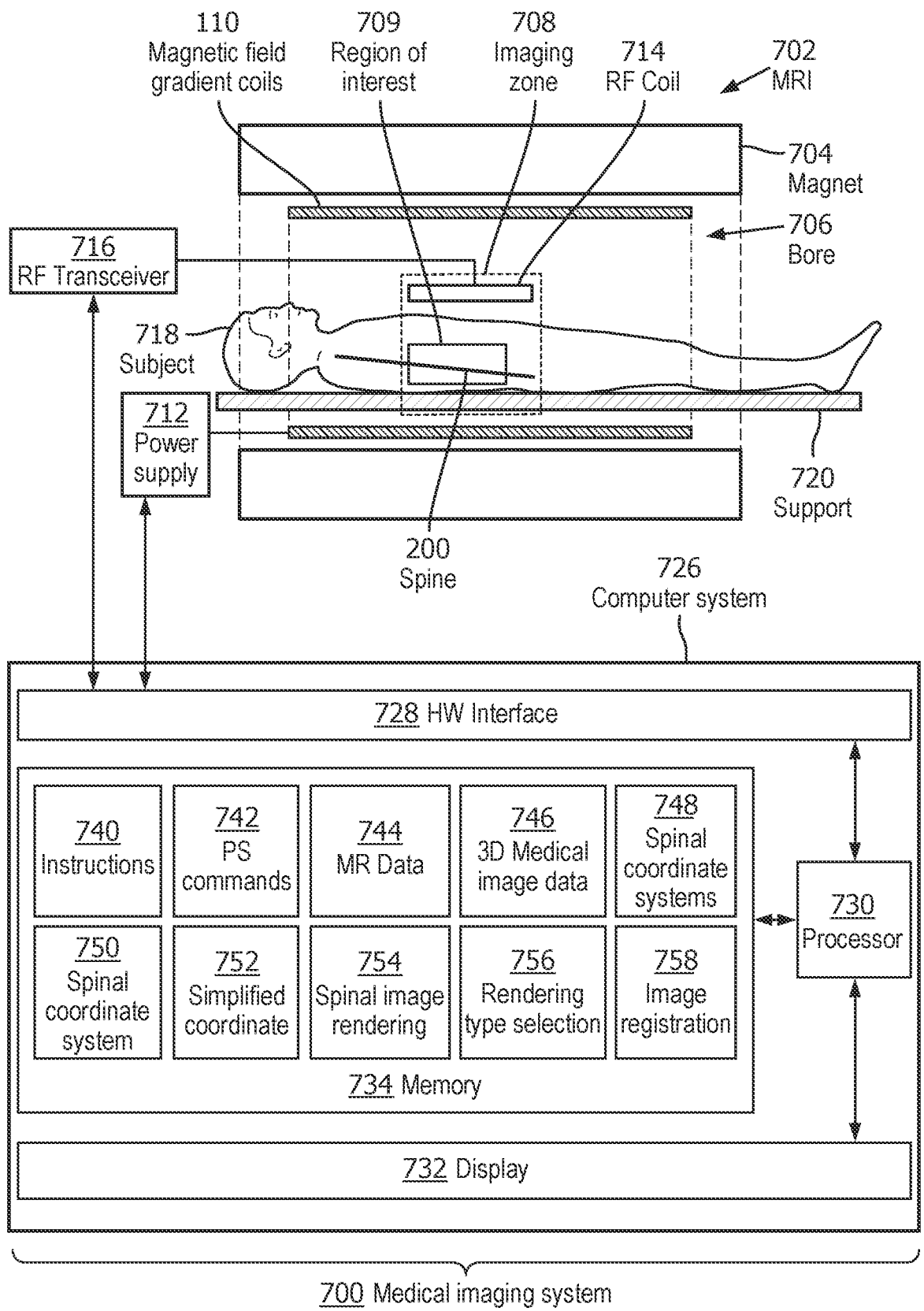
FIG. 7 illustrates a view of a magnetic resonance imaging system.

FIG. 7 shows an example of a medical imaging system 700. In the example shown in FIG. 7 the medical imaging system 700 comprises a magnetic resonance imaging system 702. The medical imaging system 700 also comprises a computer system 726. In some examples the medical imaging system 700 only comprises the computer system 726 and functions which are specific to operating the magnetic resonance imaging system 702 are not present.

The magnetic resonance imaging system 702 comprises a magnet 704. The magnet 704 is a superconducting cylindrical type magnet with a bore 706 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 706 of the cylindrical magnet 704 there is an imaging zone 708 where the magnetic field is strong and uniform enough to perform magnetic resonance imaging. A region of interest 709 is shown within the imaging zone 708. A subject 718 is shown as being supported by a subject support 720 such that at least a portion of the subject 718 is within the imaging zone 708 and the region of interest 709. The subject 718 comprises a spine 200. The spine 200 is shown as being partially within the region of interest 709.

Within the bore 706 of the magnet there is also a set of magnetic field gradient coils 710 which is used for acquisition of magnetic resonance data to spatially encode magnetic spins within the imaging zone 708 of the magnet 704. The magnetic field gradient coils 710 connected to a magnetic field gradient coil power supply 712. The magnetic field gradient coils 710 are intended to be representative. Typically magnetic field gradient coils 710 contain three separate sets of coils for spatially encoding in three orthogonal spatial directions. A magnetic field gradient power supply supplies current to the magnetic field gradient coils. The current supplied to the magnetic field gradient coils 710 is controlled as a function of time and may be ramped or pulsed.

Adjacent to the imaging zone 708 is a radio-frequency coil 714 for manipulating the orientations of magnetic spins within the imaging zone 708 and for receiving radio transmissions from spins also within the imaging zone 708. The radio frequency antenna may contain multiple coil elements. The radio frequency antenna may also be referred to as a channel or antenna. The radio-frequency coil 714 is connected to a radio frequency transceiver 716. The radio-frequency coil 714 and radio frequency transceiver 716 may be replaced by separate transmit and receive coils and a separate transmitter and receiver. It is understood that the radio-frequency coil 714 and the radio frequency transceiver 716 are representative. The radio-frequency coil 714 is intended to also represent a dedicated transmit antenna and a dedicated receive antenna. Likewise the transceiver 716 may also represent a separate transmitter and receivers. The radio-frequency coil 714 may also have multiple receive/transmit elements and the radio frequency transceiver 716 may have multiple receive/transmit channels. For example if a parallel imaging technique such as SENSE is performed, the radio-frequency could 714 will have multiple coil elements.

The transceiver 716 and the gradient controller 712 are shown as being connected to a hardware interface 728 of a computer system 726. The computer system further comprises a processor 730 that is in communication with the hardware system 128, a memory 734, and a display 732. The memory 734 may be any combination of memory which is accessible to the processor 730. This may include such things as main memory, cached memory, and also non-volatile memory such as flash RAM, hard drives, or other storage devices. In some examples the memory 730 may be considered to be a non-transitory computer-readable medium.

The computer memory 734 is shown as containing machine-executable instructions 740. The machine-executable instructions contain commands or instructions which enable the processor 730 to control the operation and function of the magnetic resonance imaging system 702. The computer memory 734 is shown as further containing pulse sequence commands 742. The pulse sequence commands 742 are either instructions or data which may be converted into instructions which enable the processor 730 to control the magnetic resonance imaging system 702 to acquire magnetic resonance data. The magnetic resonance data may for instance be used to cause the magnetic resonance imaging system to perform multiple pulse repetitions which cause magnetic resonance signals 744 to be acquired.

The computer memory 734 is shown as containing machine-executable instructions 740. The machine-executable instructions 740 enable the processor 730 to control the operation and function of the medical imaging system 700 such as the magnetic resonance imaging system 702. The computer memory 734 is further shown as containing pulse sequence commands 742 that enable the processor 730 to control the magnetic resonance imaging system 702 to acquire magnetic resonance data. The computer memory 734 is further shown as containing magnetic resonance data 744 which has been acquired by controlling the magnetic resonance imaging system 702 with the pulse sequence commands 742. The computer memory 734 is further shown as containing three-dimensional medical image data which has been reconstructed from the magnetic resonance data 744. In this case the three-dimensional medical image data is three-dimensional magnetic resonance imaging data. The three-dimensional medical image data 746 could for example be three-dimensional magnetic resonance data or it could be a collection of two-dimensional slices of magnetic resonance images.

The computer memory 734 is further shown as containing a set of spinal coordinate systems 748 each of which corresponds to the coordinate system as is depicted in FIG. 1. The computer memory 734 is further shown as containing a mapping 750 between the set of spinal coordinate systems 748 and a simplified coordinate system such as is illustrated in FIGS. 1 and 2. The computer memory 734 is further shown as containing a simplified coordinate 752 that has been received from a graphical user interface. The computer memory 734 is further shown as containing a spinal image rendering 754 which has been calculated from the three-dimensional medical image data 746, using the simplified coordinate 752 and the mapping between the spinal coordinate system 750 and the simplified coordinate system to determine how to calculate the rendering. The computer memory 734 further contains an image rendering type selection 756. The image rendering type selection 756 in some cases may be equivalent to the selection of the view plane as is illustrated in FIGS. 3-6. The computer memory 734 is further shown as containing an image registration 758. This is an image registration 758 of the spine 200. The image registration 758 may be equivalent to storing the simplified coordinates 752.

FIG. 8 depicts a graphical user interface rendered on the display 732. The graphical user interface 800 comprises several elements. There is a rendering location 802 for rendering the spinal image rendering 754. There are also a first 804, a second 806 and a third 808 simplified coordinate selector. These selectors enable the operator to explore the three-dimensional medical imaging data using the simplified coordinates. In some examples there may also be a selector which enables the operator to change the coordinates that the three selectors 804, 806, and 808 select. For example in some instances the simplified coordinates may be used and in other instances the coordinates of the three-dimensional medical image data or other coordinates system may be selected. The graphical user interface 800 is further shown as containing an image rendering type selector 810. This selector enables the operator to select how the data should be rendered on the rendering location 802. It could for example make a selection which changes how the view plane 302 is oriented such as is illustrated in FIGS. 3-6.

FIG. 9 shows a further view of the graphical user interface 800 that was illustrated in FIG. 8. The graphical user interface 800 comprises several additional elements. In this Fig. there is an additional rendering location 900 for displaying additional renderings of an additional three-dimensional medical imaging data. For example the simplified coordinate system may function as a registration of the three-dimensional medical image data. An operator could use the first 804, second 806, and third 808 simplified coordinate selector to find a position of interest in the three-dimensional medical image data. The operator could then load a different set of three-dimensional medical image data from for example the same subject or even from a different subject and use those same coordinates to render data on the additional rendering location 900.

In some examples, the operator could display different sites of information and even change the view so that it renders a different view using the additional image rendering type selector 902. This may provide great flexibility in using the simplified coordinate system for navigating spinal image data. For example the operator could use standardized medical image data and render this in the rendering location 802 for example when using the interface the same medical image data is used regardless of which subject it is. The operator is very familiar with the anatomy of the normally examined data and can quickly navigate it using the controls 804, 806, and 808. Then after an examination, the data from the subject being examined can be loaded into the additional rendering location 900 and the view can be automatically loaded into the right coordinate position.

Figure 10:
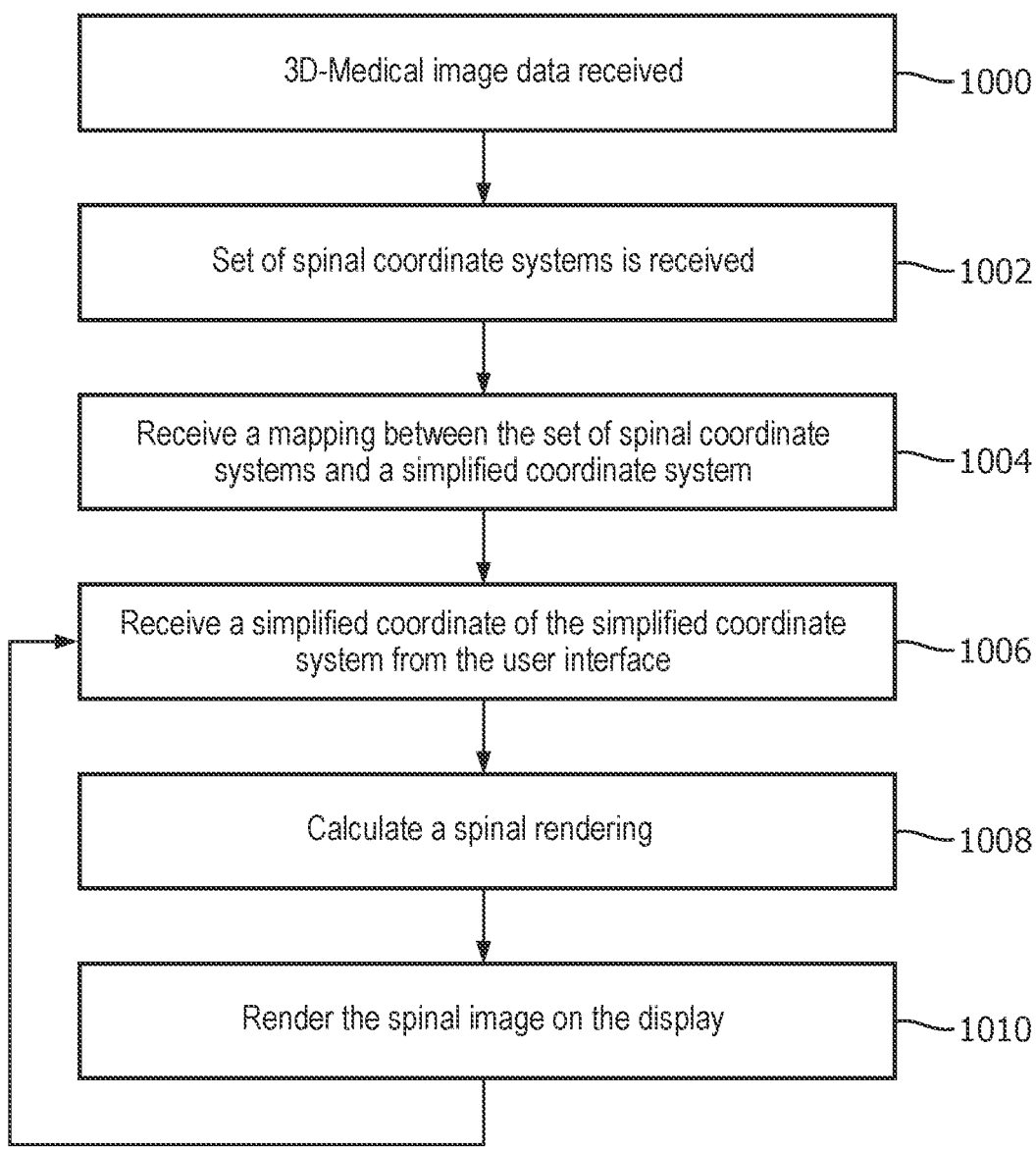
FIG. 10 shows a flow chart which illustrates a method of operating the magnetic resonance imaging system of FIG. 7.

FIG. 10 illustrates a flowchart which details a method of operating the medical imaging system 700 of FIG. 7. First in step 1000 three-dimensional medical image data 746 is received. The three-dimensional medical image data is descriptive of a region of interest 709 of the subject 718 and the region of interest 709 at least partially contains a spine 200. Next in steps 1002 a set of spinal coordinate systems 748 is received. Each is descriptive of a location and an orientation of spinal vertebrae 100 in the three-dimensional medical image data 746. The set of spinal coordinate systems 748 further comprise a set of spine center line positions 102 which are each descriptive of a position along a spine center line 108. Next in step 104 a mapping 750 between the set of spinal coordinate systems 748 and a simplified coordinate system are received. The simplified coordinate system comprises a spinal height descriptive of a position along the spine center line 108. The simplified coordinate system further comprises a rotational orientation relative to a local vertebrae orientation such as illustrated by the vectors 104 and 106. The simplified coordinate system further comprises an offset from the spine center line. Next the method proceeds to step 106, 108, and 110 which form a loop. Within this loop the method comprises receiving a simplified coordinate of the simplified coordinate system from the graphical user interface 800. After the simplified coordinate system has been received a spinal image rendering 754 is calculated. The spinal image rendering is calculated using the mapping 750.

Figure 11:
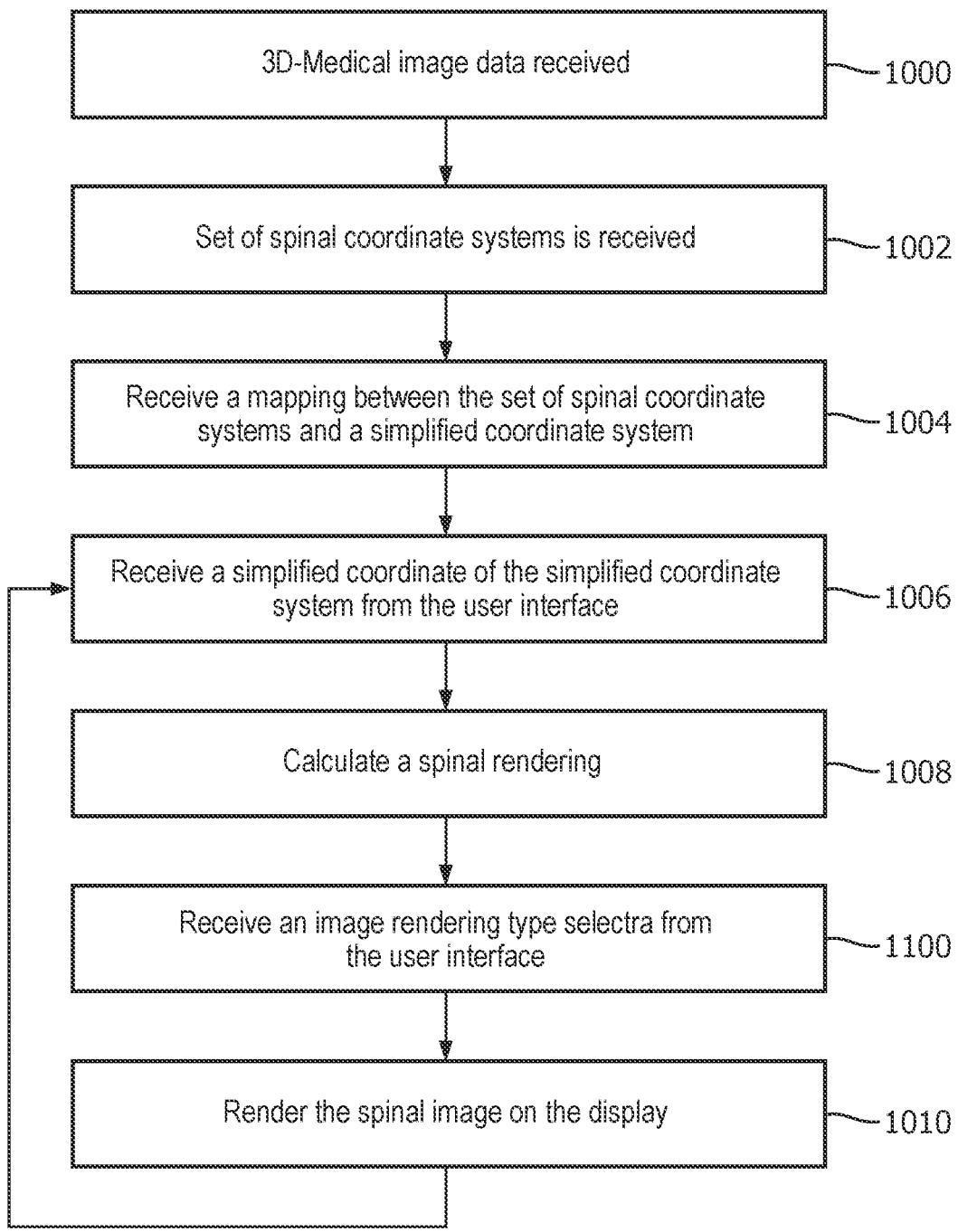
FIG. 11 shows a flow chart which illustrates an alternative method of operating the magnetic resonance imaging system of FIG. 7.

FIG. 11 shows a flowchart which illustrates a further method of using the medical imaging system 700 of FIG. 7. The method in FIG. 11 is similar to that in FIG. 10. There is an additional method step which has been added. After step 1008 has been performed step 1100 is performed. In step 1100 an image rendering type selection 756 is received from the user interface 800. Then the step proceeds again to step 1010 where the spinal image rendering is recalculated and then rendered on the graphical user interface. In the method shown in FIG. 11 the order of step 1008 and step 1100 is not critical, the two can be reversed. Also in a particular loop step 1008 or step 1100 may be also not performed in some cases.

The average length of about 70 cm, the spine is a rather large anatomical structure. For many applications, such as detection and characterization of spine bone metastasis, spinal nerves and CSF flow malfunctions, it is beneficial to examine the whole spine. Especially for pathological cases such as scoliosis, the course of the spinal column can show a high degree of curvature and curvature change along the spine making a comprehensive radiological reading of a spine case a time consuming task.

Examples may describe a spine guided visualization approach that reduces the navigational degrees of freedom for obtaining clinically informative visualizations. The user maneuvers relative to the spine geometry (along the centerline (or "spine centerline"), with a lateral offset from the centerline and a rotation around the centerline). The necessary geometrical information is obtained from a sparse set of landmarks along the spine. The approach provides an intuitive, efficient, reproducible and comparable way of spine visualization. It is compatible with curvature reducing visualization schemes like curved planar reformats (CPR), presenting at the same time an alternative if geometrical distortions associated with CPR like renderings are prohibitive.

Magnetic Resonance Imaging (MRI) with its great soft tissue contrast is an indispensable tool in today's clinical practice. With more than 25% percent of all MRI examinations, spine applications represent a major diagnostic application branch, which can benefit from further improvements.

Examples may allow to reduce substantially the navigation effort required for reading a spine case. The remaining degrees of freedom are related to the individual spine geometry of the patient. Manipulation is therefore intuitive and efficient. Due to the relation to the individual spine geometry, the approach allows the visual coupling of several datasets, without the need for identical image geometries. This is of value for follow-up examinations, multi-modal examinations, or examinations using a different patient pose (e.g. prone/supine). In that respect, this ID could be helpful to make readings more comparable and to potentially "standardize" spine-reading procedures.

Examples may also provide for an image viewing system that provides spine geometry guided visualization functionality, effectively reducing the degrees of freedom (DOF) necessary to create a rending of clinical value mitigating the above mentioned problems or disadvantages.

Examples may use an appropriate coordinate system for visualization, moving from the ordinary image coordinates (mainly determined by the acquisition process) to patient centric spine coordinates (defined by spinal cord centerline and local vertebra orientation).

After choosing a principle rendering mode (e.g., spine guided multi-planar reformat (MPR) or curved planar reformat), the user manipulates interactively the following spine related DOFs:
  Spine height level
  Anterior-posterior and left-right offset from centerline
  Rotation around centerline Based on the spine geometry information, these spine related DOFs are translated into the detailed DOFs required to define the corresponding (e.g. ortho-view like, MPR or CPR based) rendering.

Possible input to the post-processing system:
  On one or more 3D or multi-slice spine images (examples: T1 weighted image, T1 and T2 weighted image of same exam, base-line and follow up).
  Sparse spine geometry information (examples: a set of centreline points along the spinal column, a set of centreline points with associated local anterior-posterior direction vector, a set of centreline points with vertebra level label). Typically, the geometry information is provided by an automated anatomy localization functionality. In some examples, a fall-back option can also be provided in an interactive or semi-automated fashion.

The following geometrical information about the spine may taken into account in some examples. It can be provided by an automated anatomical landmark localization algorithm (being the ultimate goal) but can also be manually defined, using a few user interactions:
  The course of the spinal column from foot to head, e.g. represented by a sparse set of spinal cord centerline points (1 point for each vertebra being sufficient)
  The local anterior-posterior direction vector associated to each spinal cord centerline point (alternatively a set of landmarks at the posterior tip of the spinous process can be used (see FIG. 1 below).)
  Height level information, e.g. the vertebra type (C1, ... , L5, S1) for a given centerline point This coarse representation of spine geometry may be converted into a dense series of coordinate systems following the course of the spinal column (see also FIG. 3). The distance of coordinate systems should be in the order of the pixel size of the final rendering. It provides for an arbitrary column height level the tangential vector of the spine centerline and the local anterior-posterior (AP) (104 in FIG. 1) and local left-right (LR) (106 in FIG. 1) direction vectors of the current vertebra.

The key point of the system is, that the spine data can be explored relative to the local spine geometry (see FIG. 2):
  Height level (position along spine centerline—300 positioned 108 in FIGS. 3-6)
  Lateral AP and LR offset relative to the spine centre in a plane orthogonal to the centerline
  Rotation around the centerline or chose offset position.

Figure 12:
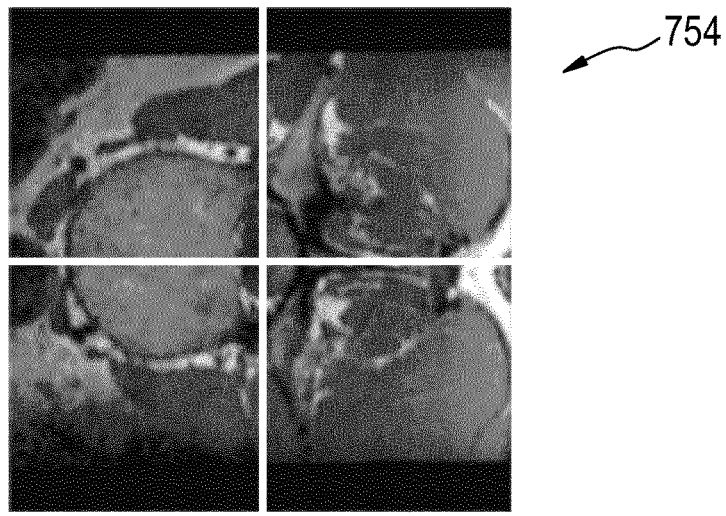
FIG. 12 shows a view of a spinal image rendering.

FIG. 12 shows an example of a spinal image rendering 754. The spinal image rendering 754 for example may use a view plane 302 such as illustrated in FIG. 3.

Figure 13:
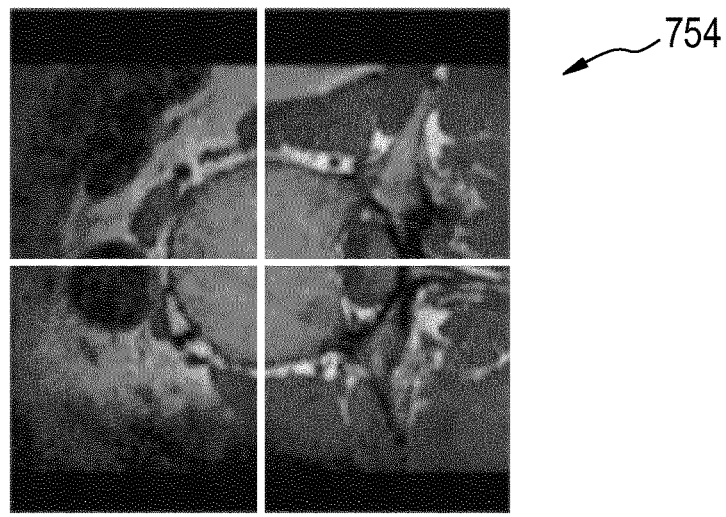
FIG. 13 shows a view of an alternative spinal image rendering.

FIG. 13 shows the spinal image rendering 754 at the same spinal height as was shown in FIG. 12 except in FIG. 13 the image has been offset from the spinal center line 108.

Figure 14:
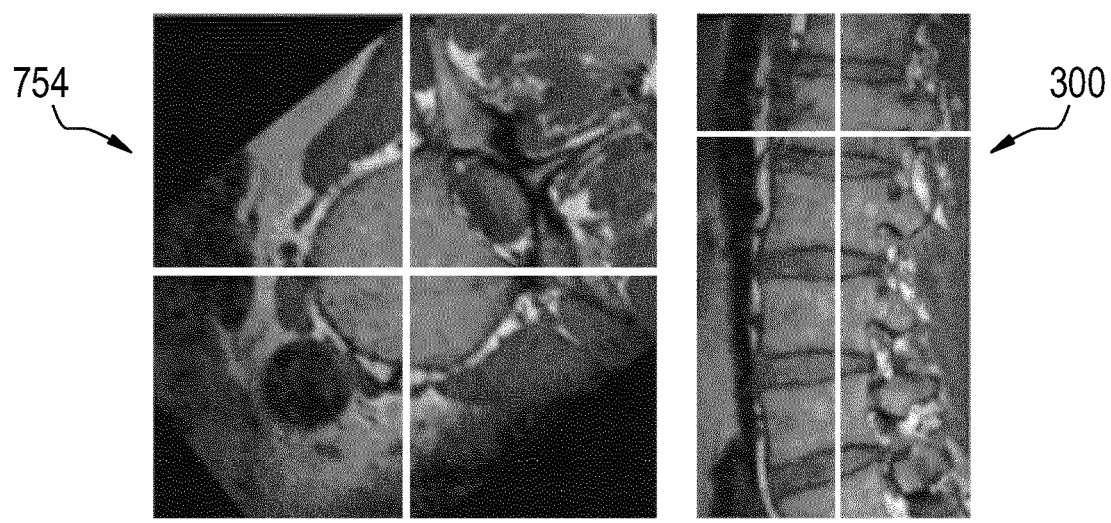
FIG. 14 shows a view of an alternative spinal image rendering.

FIG. 14 shows a further rendering of the spinal image rendering 754 of FIGS. 12 and 13. In this example the rendering shows an example of an offset and a rotation. The Fig. to the right of the rendering 754 illustrates the location of the spinal height 300 in the dataset.

Based on the internal dense representation of local spine position and orientation, a wide range of spine visualization modes can be realized.

Depending on the clinical need, it may be crucial to obtain a single view depicting the whole spine using a curved planer reformat. This can be obtained by projecting-out the spine curvature in view direction ('half CPR') or in total, converting the spine into a virtually straight line ('full CPR'). These rendering modes necessarily go along with geometrical distortions.

The method explained here may provide for an intuitive and efficient approach for spine viewing even in cases where rendering induced geometrical distortions are prohibitive. It does so by translating low dimensional intuitive maneuvering actions (height level change, lateral offset change, rotation around centerline) into the multi-planar reformation actions needed to realize the respective view.

The following list comprises some possible rendering modes supported (list not exhaustive):

TABLE 1

Examples for supported rendering modes.

| Rendering mode | Remark | Distortion |
| --- | --- | --- |
| Conventional unguided orthoview | Free navigation, no spine support | no distortion |
| Spine guided ortho-view, axis parallel | Position of cross-hair is guided by spine centreline, orientation of cross-hair is image axis aligned | no distortion |
| Spine guided ortho-view, oblique | Position of cross-hair is guided by spine centreline, orientation of cross-hair is guided by local coordinate system (local AP and LR direction) | no distortion |
| Half planar reformat | Spine centreline projected into view plane, curvature still visible in orthogonal view | mild distortion |
| Full planar reformat | Spine centreline becomes straight line | Strong distortion |

Some examples could depict the use of a dense set of coordinate systems to represent the spine geometry. It would not be necessary to have a spine center positions defined for every vertebrae. In some examples the coordinate system and spine center position for predetermined vertebrae could be used.

In general, based on anatomical landmarks and vectors, a set of coordinate systems could be generated by spline based interpolation representing the true spine course. Here, for visualization, only every 8th coordinate system is show. In this example, the rending mode is 'half CPR', meaning that the curvature of the spine in one direction is removed (e.g., the spine centerline is projected onto a plane, here the mid-sagittal plane at cross-hair position). This could lead to an apparently straight line of coordinate system used for rending. Only apparently, because coordinate systems still follow the in-plane curvature of the spine, not visible from that angle.

Figure 15:
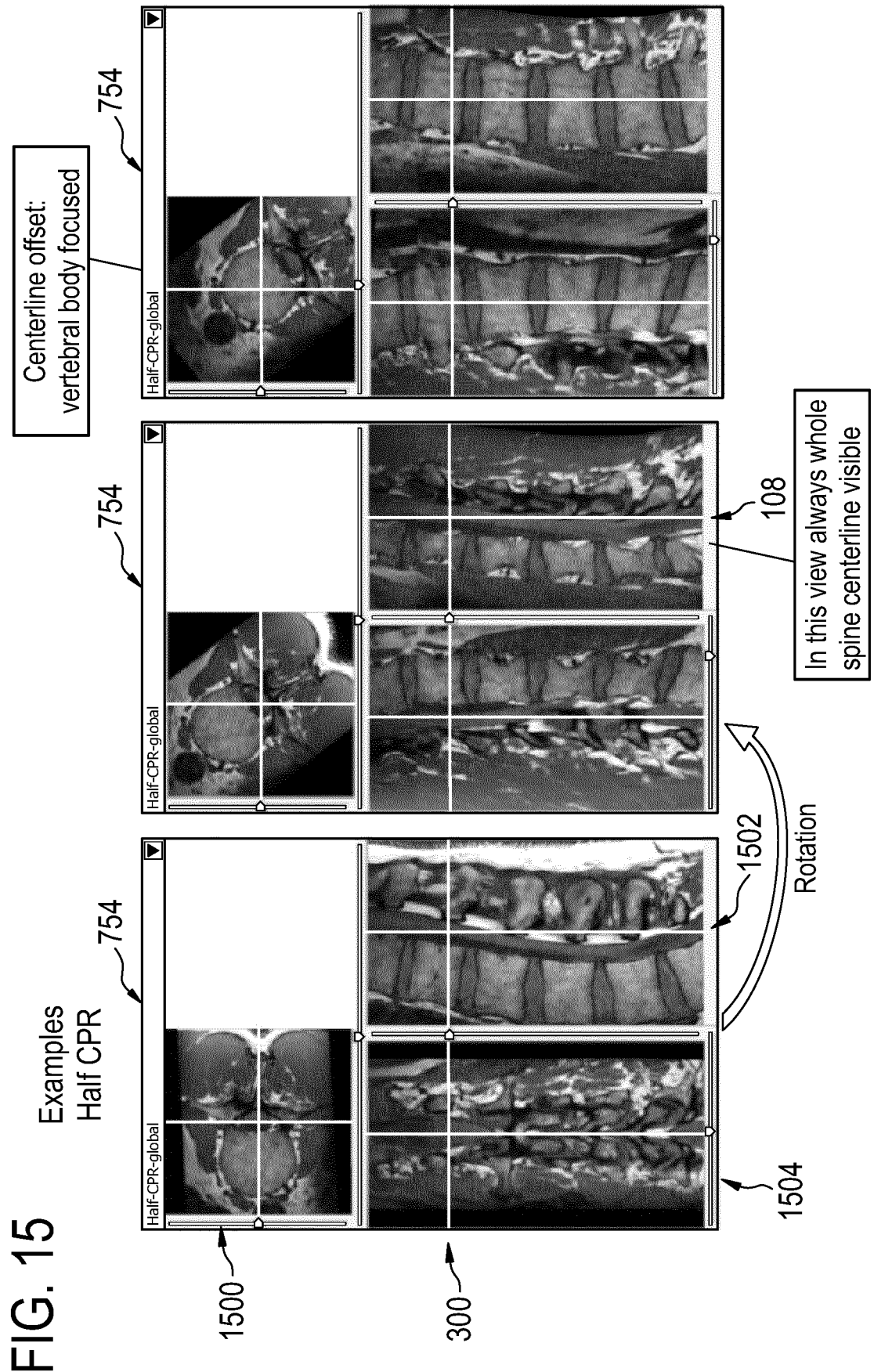
FIG. 15 shows a view of an alternative spinal image rendering.

FIG. 15 shows three examples of spinal image renderings 754. In each case three views are shown. The views use the cross-section perpendicular 1500 to the spine center line 108, a view which shows a cross-sectional view of the spine 200 such as illustrated in FIGS. 3-6 1502. A final view 1504 always shows in the so called half planar reformat 1504 such as used by the view plane 302 in FIG. 6.

FIG. 15 Illustrates the effect of setting the lateral offset to the centre of the vertebral bodies. Changing subsequently the rotation DOF still keeps the vertebral bodies centered in the display.

Figure 16:
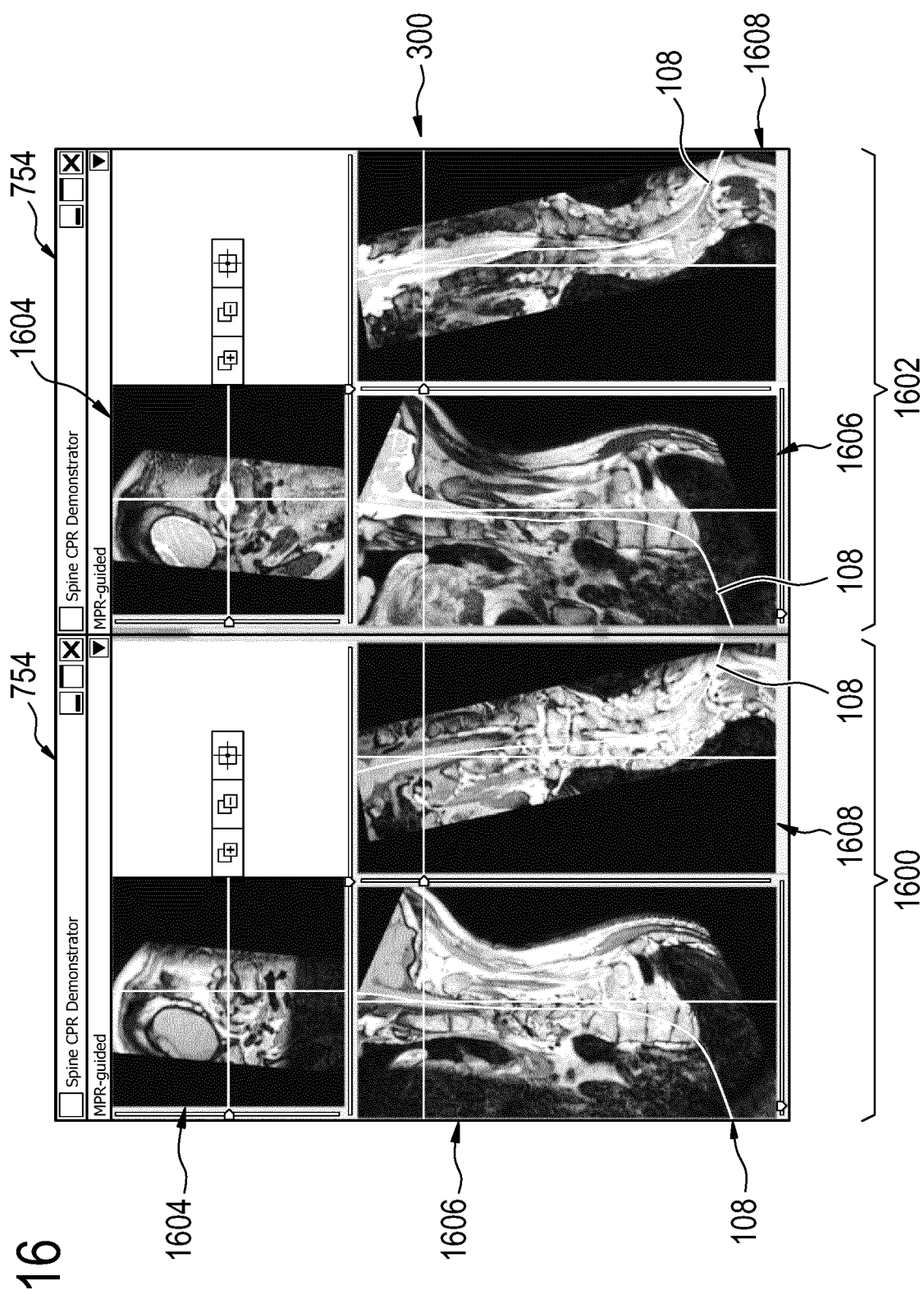
FIG. 16 shows a view of an alternative spinal image rendering.
Figure 17:
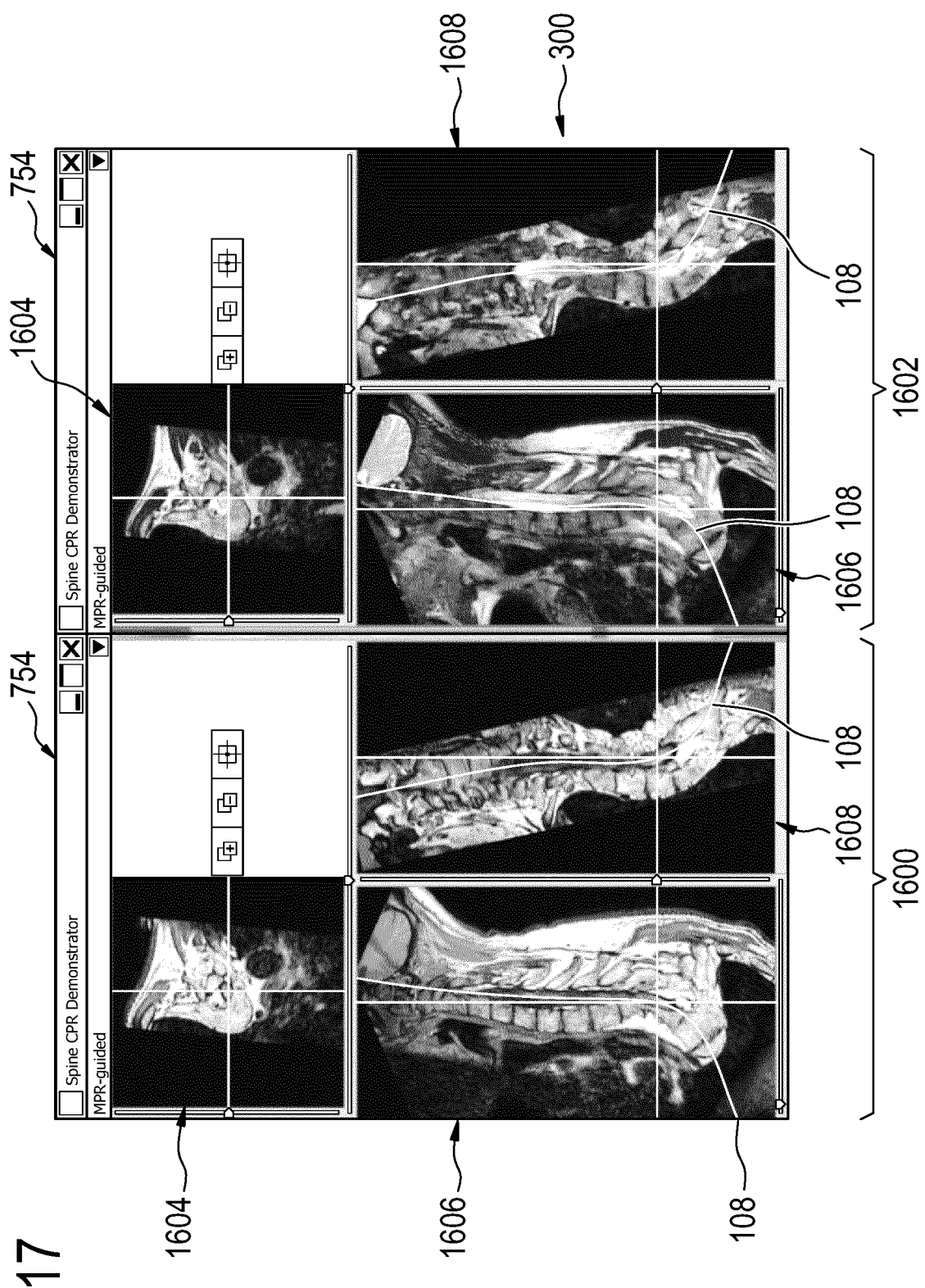
FIG. 17 shows a view of an alternative spinal image rendering.

FIGS. 16 and 17 show rending types for spine guided MPR. Shown is a scoliosis case with simultaneous display of T1 weighted (left) 1600 and T2 weighted images (right) 1602, rendering cross-section (top views) 1604, local AP views (left) 1606 and local LR views (right) 1608 for two different height levels. Changing the height level still keeps visualization vertebra centered and oriented.

Figure 18:
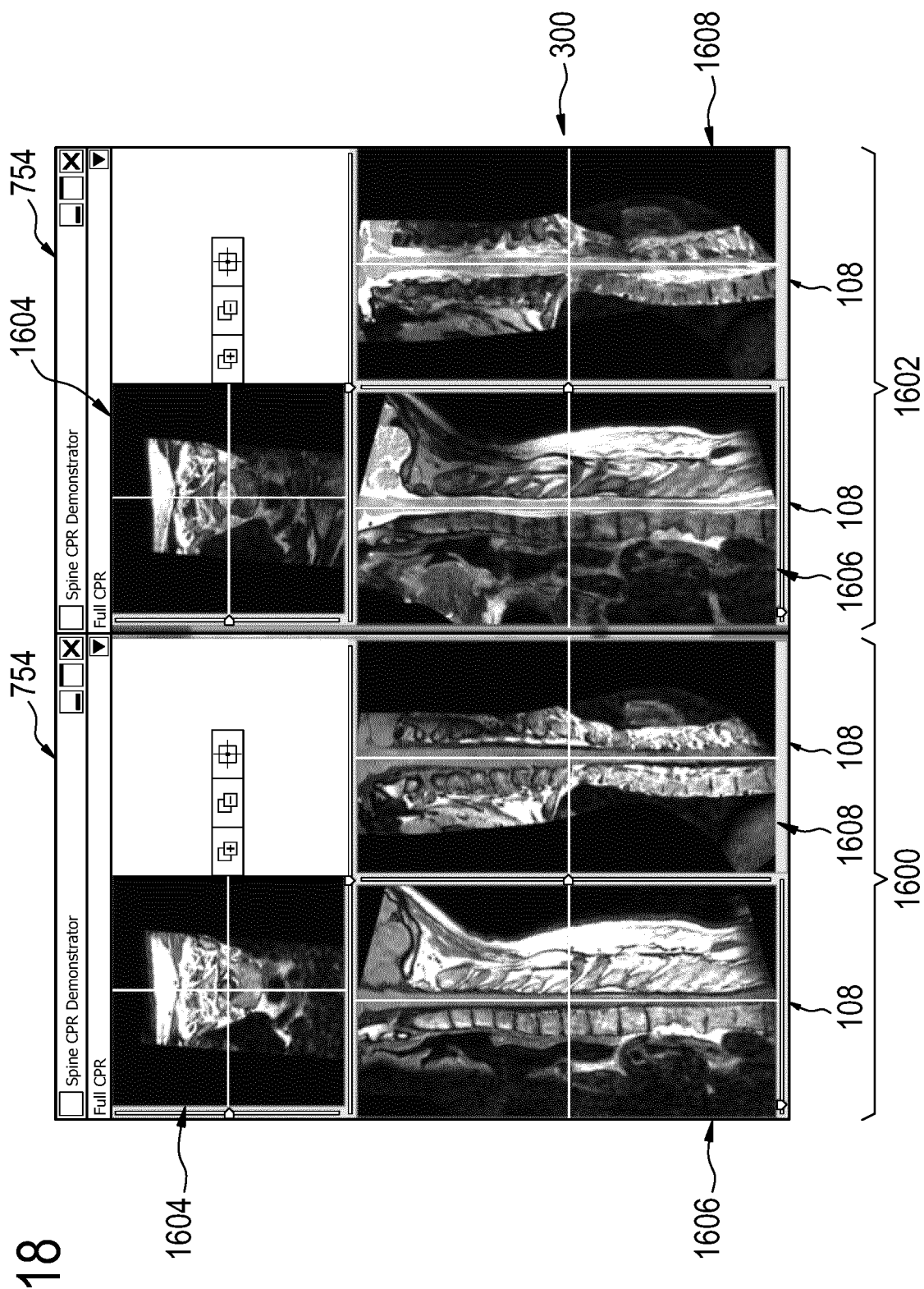
FIG. 18 shows a view of an alternative spinal image rendering.

FIG. 18. shows a rending type for full CPR. Shown is a scoliosis case with simultaneous display of T1 weighted (left) 1600 and T2 weighted images (right) 1602, rendering cross-section (top views) 1604, local AP views (left) 1606 and local LR views (right) 1608. For full CPR, both head-foot oriented orthogonal views show the whole centerline (or a respective offset position).

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 vertebrae
102 spine centerline position
104 first axis
106 second axis
108 spine centerline
200 spine
300 spinal height
302 view plane
500 coordinate system of three dimensional medical data
700 medical imaging system
702 magnetic resonance imaging system
104 magnet
106 bore of magnet
108 imaging zone
109 region of interest
110 magnetic field gradient coils
112 magnetic field gradient coil power supply
114 radio-frequency coil
116 transceiver
118 subject
120 subject support
126 computer system
128 hardware interface
130 processor
732 display
734 computer memory
740 machine executable instructions
742 pulse sequence commands
744 magnetic resonance data
746 three dimensional medical image data
748 set of spinal coordinate systems
750 mapping between set of spinal coordinate systems and a simplified coordinate system
752 simplified coordinate
754 spinal image rendering
756 image rendering type selection
758 image registration
800 graphical user interface
802 rendering location
804 first simplified coordinate selector
806 second simplified coordinate selector
808 third simplified coordinate selector
810 image rendering type selector
900 additional rendering location
902 additional image rendering type selector
1500 perpendicular to spine centerline
1502 cross sectional view of spine
1504 half planar reformat
1600 T1 weighted images
1602 T2 weighted images
1604 cross sectional view
1606 anterior-posterior view
1608 left-right view

The invention claimed is:

1. A medical imaging system comprising:
a memory configured to store machine executable instructions;
a display configured to render a user interface;
a processor, wherein execution of the machine executable instructions causes the processor to:
receive three dimensional medical image data descriptive of a region of interest of a subject, wherein the region of interest comprises a spine;
receive a set of spinal coordinate systems each descriptive of a location and an orientation of spinal vertebrae in the three dimensional medical image data, wherein the set of spinal coordinate systems further comprises a set of spine centerline positions each positioned on a spine centerline; and receive a mapping between the set of spinal coordinate systems and a simplified coordinate system, wherein the simplified coordinate system comprises a spinal height descriptive of a position along the spine centerline, wherein the simplified coordinate system further comprises a rotational orientation relative to a local vertebrae orientation, wherein the simplified coordinate system further comprises an offset from the spine centerline; and wherein execution of the machine executable instructions further cause the processor to repeatedly:

receive a simplified coordinate of the simplified coordinate system from the user interface;

calculate a spinal image rendering, wherein calculating the spinal image rendering comprises using the mapping to transform the simplified coordinate into the set of spinal coordinate systems to determine an image location in the three dimensional medical image data; and render the spinal image rendering on the display, wherein the medical imaging system is configured for user navigation through the three-dimensional medical data by means of the simplified coordinate system.

2. The medical imaging system of claim 1, wherein execution of the machine executable instructions further cause the processor to repeatedly:

receive an image rendering type selection from the user interface; and recalculate the spinal image rendering using the image rendering type selection.

3. The medical imaging system of claim 2, wherein the image rendering type is any one of the following: an orthographic view with freely chosen axes, an orthographic view with an axis aligned with the three dimensional data, and an orthographic view with an axis aligned with the spine centerline position at the spinal coordinate.

4. The medical imaging system of claim 1, wherein execution of the machine executable instructions further cause the processor to receive a location registration selection from the user interface, wherein execution of the machine executable instructions further cause the processor to store the simplified coordinate as an image registration.

5. The medical imaging system of claim 4, wherein execution of the machine executable instructions further cause the processor to receive additional three dimensional image data descriptive of an additional region of interest of the subject, wherein the region of interest comprises the spine, wherein execution of the machine executable instructions further cause the processor to:

receive additional three dimensional medical image data descriptive of the region of interest of the subject, wherein the region of interest comprises the spine;

receive an additional set of spinal coordinate systems equivalent to the set of spinal coordinate systems; and receive an additional mapping, wherein the additional mapping is between the additional set of spinal coordinate systems and the simplified coordinate system.

6. The medical imaging system of claim 5, wherein execution of the machine executable instructions causes the processor to:

calculate an additional spinal image rendering, wherein calculating the additional spinal image rendering comprises using the additional mapping to transform the simplified coordinate into the additional set of spinal coordinate systems to determine an additional image location in the additional three dimensional medical image data; and render the additional spinal image rendering on the display.

7. The medical imaging system of claim 1, wherein the set of spinal coordinates and the mapping is received as input from the user interface.

8. The medical imaging system of claim 1, wherein execution of the machine executable instructions further causes the processor to:

calculate a segmentation of the three dimensional medical image data using a segmentation algorithm; and calculate the set of spinal coordinate systems and/or the mapping using the segmentation.

9. The medical imaging system of claim 1, wherein the three dimensional medical image data is any one of the following: a three dimensional data set and a stack of two dimensional slices.

10. The medical imaging system claim of claim 1, wherein the medical imaging system further comprises a magnetic resonance imaging system, wherein the processor is configured for controlling the magnetic resonance imaging system, wherein the memory further comprises pulse sequence commands, wherein the pulse sequence commands comprise commands for controlling the magnetic resonance imaging system to acquire the three dimensional medical image data according to a magnetic resonance imaging protocol, wherein the three dimensional image data is magnetic resonance imaging data, wherein execution of the machine executable instructions further cause the processor to receive the three dimensional medical image data by reconstructing the three dimensional medical image data from the magnetic resonance data.

11. The medical imaging system of claim 1, wherein the three dimensional image data is any one of the following: a T1 weighted image, a T2 weighted image, and a composite T1 and T2 weighted image.

12. The medical imaging system of claim 1, wherein the medical imaging system further comprises a computed tomography system, and wherein the three-dimensional image data is computed tomography image data.

13. A medical imaging method, wherein the method comprises:

receiving three dimensional medical image data descriptive of a region of interest of a subject, wherein the region of interest comprises a spine;

receiving a set of spinal coordinate systems each descriptive of a location and an orientation of spinal vertebrae in the three dimensional medical image, wherein the set of spinal coordinate systems further comprises a set of spine centerline positions each positioned on a spine centerline; and receiving a mapping between the set of spinal coordinate systems and a simplified coordinate system, wherein the simplified coordinate system comprises a spinal height descriptive of a position along the spine centerline, wherein the simplified coordinate system further comprises a rotational orientation relative to a local vertebrae orientation, wherein the simplified coordinate system further comprises an offset from the spine centerline; and wherein the method further comprises repeatedly:

receiving a simplified coordinate of the simplified coordinate system from the user interface;

calculating a spinal image rendering, wherein calculating the spinal image rendering comprises using the mapping to transform the simplified coordinate into the set of spinal coordinate systems to determine an image location in the three dimensional medical image data; and rendering the spinal image rendering on the display such that user navigation through the three-dimensional medical data is performed by means of the simplified coordinate system.

14. A computer program product comprising machine executable instructions stored on a non-transitory computer readable medium for execution by a processor, wherein execution of the machine executable instructions causes the processor to:

receive three dimensional medical image data descriptive of a region of interest of a subject, wherein the region of interest comprises a spine;

receive a set of spinal coordinate systems each descriptive of a location and an orientation of spinal vertebrae in the three dimensional medical image, wherein the set of spinal coordinate systems further comprises a set of spine centerline positions each positioned on a spine centerline; and receive a mapping between the set of spinal coordinate systems and a simplified coordinate system, wherein the simplified coordinate system comprises a spinal height descriptive of a position along the spine centerline, wherein the simplified coordinate system further comprises a rotational orientation relative to a local vertebrae orientation, wherein the simplified coordinate system further comprises an offset from the spine centerline; and wherein execution of the machine executable instructions further cause the processor to repeatedly:

receive a simplified coordinate of the simplified coordinate system from the user interface, wherein the simplified coordinate comprises at least the spinal height;

calculate a spinal image rendering, wherein calculating the spinal image rendering comprises using the mapping to transform the simplified coordinate into the set of spinal coordinate systems to determine an image location in the three dimensional medical image data; and render the spinal image rendering on a display, wherein the computer program product is configured for user navigation through the three-dimensional medical data by means of the simplified coordinate system.

15. The computer program product of claim 14, wherein execution of the machine executable instructions further cause the processor to repeatedly: receive an image rendering type selection from the user interface; and recalculate a spinal image rendering using the image rendering type selection.

* * * * *